United States Patent [19]
Ax et al.

[11] Patent Number: 5,434,139
[45] Date of Patent: Jul. 18, 1995

[54] DETECTION OF HEPARIN-BINDING SEMINAL PLASMA PROTEINS

[75] Inventors: Roy L. Ax, Middleton, Wis.; David J. Miller, Houston, Tex.; Martin A. Winer, New York, N.Y.

[73] Assignee: Wisconsin Alumni Research Foundation, Madison, Wis.

[21] Appl. No.: 5,869

[22] Filed: Jan. 15, 1993

Related U.S. Application Data

[63] Continuation of Ser. No. 386,954, Jul. 28, 1989, abandoned.

[51] Int. Cl.$^6$ .................. A61K 37/02; C07K 15/06; G01N 33/50
[52] U.S. Cl. ........................... 514/21; 436/86; 436/503; 436/906; 530/350; 530/852
[58] Field of Search ............... 514/21, 12, 8; 530/350, 530/399, 850, 852, 395, 396; 424/520, 559, 561; 600/33; 435/806, 2; 436/906, 503, 504, 63, 86, 87

[56] References Cited

U.S. PATENT DOCUMENTS

| | | | |
|---|---|---|---|
| 4,446,122 | 5/1984 | Chu et al. | 435/240.27 |
| 4,767,703 | 8/1988 | Ax et al. | 435/29 |

OTHER PUBLICATIONS

Feig et al., Proc. Nat. Acad. Sci., USA, vol. 77 No. 8 pp. 4774–4778, 1980.
Bellve et al., Aminals New York Acad. Sci., vol. 564, Jul. 1989, pp. 116–131.
Braunhut et al. Biology Reprod., vol. 42, No. 4 pp. 639–648 (1990).
Bellve et al., Rec. Prog. Horm. Des., vol. 40 pp. 531–567 (1984).
Chemical Engineering, Issued Feb. 18, 1985, Bjurstrom, "Biotechnology", pp. 126, 157, 158.
Biochem. Biophys. Res. Comm., vol. 153, No. 1, issued May 31, 1988, Hurst et al, "The Identification of a Heparin-Binding Protein . . . ", pp. 289–293.
Miller, et al., 1987, "Isolation and Characterization of Seminal Fluid Proteins That Bind Heparin. Proc. Regulation of Ovarian and Testicular Function," *Adv. Exp. Med. Biol.*, 219:597–601.
Ax, R. L., et al., 1987, "Glycosaminoglycans as Probes to Monitor Differences in Fertility of Bulls," *J. Dairy Sci.*, 70:1477.
First, N. L., et al., 1987, "In-Vitro Fertilization of Ruminants," *J. Reprod. Fert.*, 34(Suppl):151–165.
Florman, H. M., et al., 1988, "The Regulation of Acrosomal Exocytosis. I. Sperm Capacitation is Required for the Induction of Acrosome Reactions by the Bovine Zona Pellucida In Vitro," *Dev. Biol.*, 128:453–463.
Florman, H. M., et al., 1988, "Regulation of Acrosomal Exocytosis. II. The Zona Pellucida-Induced Acrosome Reaction of Bovine Spermatozoa is Controlled by Extrinsinc Positive Regulatory Elements," *Dev. Biol.*, 128:464–473.

(List continued on next page.)

*Primary Examiner*—Jeffrey E. Russel
*Attorney, Agent, or Firm*—Ross & Stevens

[57] ABSTRACT

A method is disclosed relating to the isolation and purification of certain heparin-binding protein compositions in the seminal plasma of male mammals. The isolated proteins are useful in fertility studies and in enhancing the acrosomal reaction, capacitation and subsequent fertility of sperm cells.

8 Claims, 12 Drawing Sheets

OTHER PUBLICATIONS

Handrow, R. P., et al., 1982, "Structural Comparisons Among Glycosaminoglycans to Promote an Acrosome Reaction in Bovine Spermatozoa," *Biochem. Biophys. Res. Comm.*, 107:1326–1332.

Handrow, et al., 1987, "Specific Binding of the Glycosaminoglycan $^3$H–heparin to Bull, Monkey and Rabbit Spermatozoa In Vitro," *J. Androl.*, 5:51–63.

Lee, C. N., et al., 1984, "Concentrations and Composition of Glycosaminoglycans in the Bovine Reproductive Tracts," J. Dairy Sci., 67:2006–2009.

Lee, C. N., et al., 1986, "Glycosaminoglycans in Ewe Reproductive Tracts and Their Influence on Acrosome Reactions in Bovine Spermatozoa In Vitro," *J. Anim. Sci.*, 63:861–867.

Lenz, R. W., et al., 1982, "Proteoglycan from Bovine Follicular Fluid Enhances an Acrosome Reaction in Bovine Spermatozoa," *Biochem. Biophys. Res. Com.*, 106:1092–1098.

Lenz, R. W., et al., 1983, "Chondroitin Sulfate Facilitates an Acrosome Reaction in Bovine Spermatozoa as Evidenced in Light Microscopy, Electron Microscopy and In Vitro Fertilization," *Biol. Reprod.*, 284:683–690.

Lenz, R. W., et al., 1983, "Rabbit Spermatozoa Undergo An Acrosome Reaction in the Presence of Glycosaminoglycans," *Gamete Res.*, 8:11–19.

Meizel, S., et al., 1986, "Glycosaminoglycans Stimulate the Acrosomal Reaction of Previously Capacitated Hamster Sperm," *J. Exp. Zool.*, 237:134–139.

Miller and Ax, 1989, "Chemical N–Desulfation of Heparin Negates Its Ability to Capacitate Bovine Spermatozoa," Gamete Research, 23:451–465. (The contents of this journal article were presented as a seminar topic in 1988 at the *Ann. Mtg. of Amer. Assn. Advancement Sci.*, Abstr. A–10).

Parrish, et al., 1988, "Capacitation of Bovine Sperm by Heparin," *Biol. Reprod.*, 38:1171–1180.

Parrish, et al., 1989, "Capacitation of Bovine Spermatozoa by Oviduct Fluid," Biol. Reprod., 40:1020–1025.

Reyes, R., et al., 1984, "Glycosaminoglycan Sulfate as Acrosome Reaction–Inducing Factor of Follicular Fluid", *Arch. Androl.*, 12:203–209.

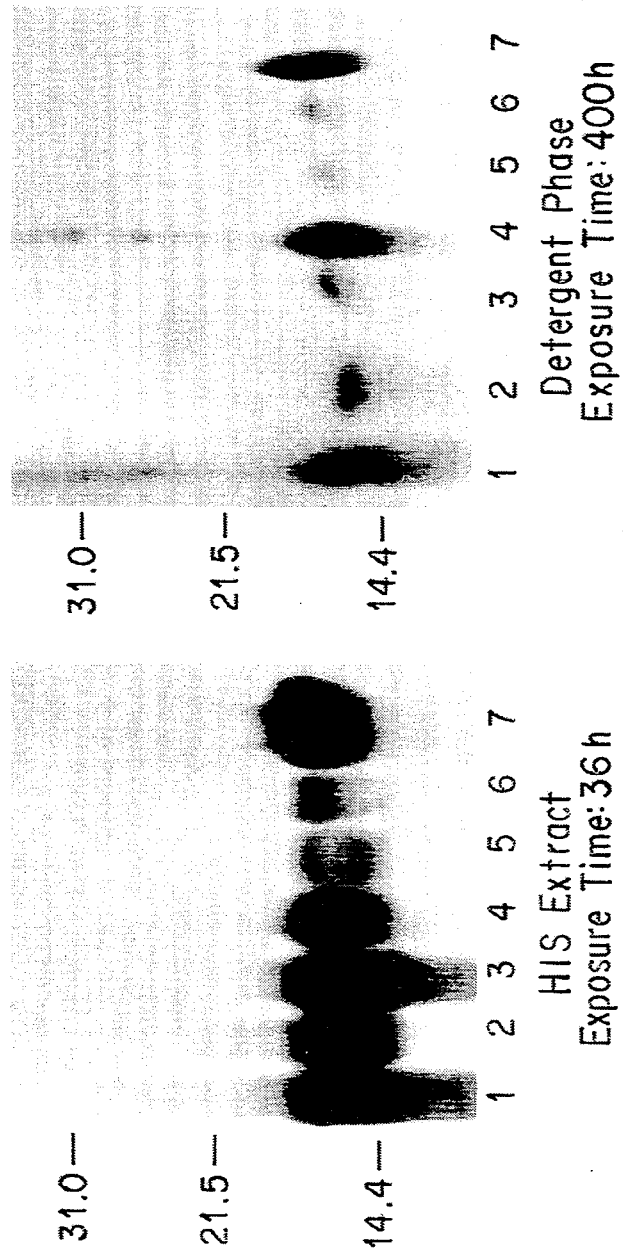

DETECTION OF HEPARIN-BINDING SEMINAL PLASMA PROTEINS

This invention was made with United States government support awarded by the United States Department of Agriculture, Grant number: 85-CRCR-1-18-64. The United States Government has certain rights in this invention.

This is a continuation of application Ser. No. 07/386,954 filed on Jul. 28, 1989, now abandoned.

FIELD OF THE INVENTION

The present invention relates to the identification of certain proteins in the seminal plasma of male mammals in general and, in particular, to the isolation and purification of classes of proteins in the seminal plasma which bind to heparin. The present invention also relates to the use of heparin-binding seminal plasma proteins in testing fertility, increasing fertility of males, decreasing fertility in males and providing a test kit which can be used to diagnose fertility status in males.

DESCRIPTION OF THE PRIOR ART

Before mammalian spermatozoa are able to fertilize a female ova, they must undergo cellular changes to acquire fertilizing potential. The result of these cellular changes is called "capacitation." Bedford, J. M. (1970), "Sperm Capacitation and Fertilization in Mammals," *Biol. Reprod.*, Suppl. 2, 128–158. After capacitation has occurred, spermatozoa undergo an acrosome reaction, a fenestration of the plasma and outer acrosomal sperm membranes with concomitant release of enzymes which facilitate penetration of the egg. Determination of the components which contribute to capacitation and the acrosome reaction in vivo is an active research area since it is known that spermatozoa must undergo these cellular changes in the male and female reproductive tract in order to acquire fertilizing potential.

It has previously been determined that bovine spermatozoa can be capacitated in vitro when they are incubated with a proteoglycan composed of a protein core to which glycosaminoglycan (GAG) linear unbranched repeating disaccharide chains are attached. It is also known that the reproductive tract fluid of several species is a rich source of GAGs (Lee, C. N. and R. L. Ax, 1984, "Concentrations and Composition of Glycosaminoglycans in the Bovine Reproductive Tract," *J. Dairy Sci.*, 67:2006–2009; Lee, C. N., et al., 1986, "Glycosaminoglycans in Ewe Reproductive Tracts and their Influence on Acrosome Reactions in Bovine Spermatozoa In Vitro," *J. Anim. Sci.*, 63:861–867). GAGs from ovarian follicular fluid and other sources stimulate the appearance of acrosome reactions in bovine, rabbit, pig and hamster sperm (Lenz, R. W., et al., 1982, "Proteoglycan from Bovine Follicular Fluid Enhances an Acrosome Reaction in Bovine Spermatozoa," *Biochem. Biophys. Res. Com.*, 106:1092–1098; Lenz, R. W., et al., 1983a, "Chondroitin Sulfate Facilitates an Acrosome Reaction in Bovine Spermatozoa as Evidenced by Light Microscopy, Electron Microscopy and In Vitro Fertilization," *Biol Reprod.*, 284:683–690; Lenz, R. W., et al., 1983b, Rabbit Spermatozoa Undergo An Acrosome Reaction in the Presence of Glycosaminoglycans," *Gamete Res.* 8:11-19; Reyes, R., et al., 1984, "Glycosaminoglycan Sulfate as Acrosome Reaction-Inducing Factor of Follicular Fluid, *Arch. Androl.*, 12:203–209; Meizel, S. and K. O. Turner, 1986, "Glycosaminoglycans Stimulate the Acrosomal Reaction of Previously Capacitated Hamster Sperm," *J. Exp. Zool.*, 237:134–139).

Seminal plasma also alters the response of spermatozoa to GAGS. (Lee, et al., 1986, supra; Florman, H. M. and N. L. First, 1988b, "The Regulation of Acrosomal Exocytosis. II. The Zona Pellucida-Induced Acrosome Reaction of Bovine Spermatozoa is Controlled by Extrinsic Positive Regulatory Elements," *Dev. Biol.*, 128:464–473). This is summarized in FIG. 1 which illustrates the kinetics of capacitation and acrosome reactions of cauda epididymal and ejaculated spermatozoa. In FIG. 1, it can be seen that bovine epididymal spermatozoa incubated with GAGs require 22 hours to undergo acrosome reactions (Lenz, et al., 1982, supra; Lenz, et al., 1983a, supra; Handrow, et al., 1982, supra). However, ejaculated spermatozoa acrosome react in 9 hours in the presence of GAGs (Handrow, et al., 1982, supra; Lenz, et al., 1982, supra). If epididymal spermatozoa are exposed to seminal plasma for 20 minutes, the seminal plasma is washed out and GAGs are added, acrosome reactions occur in 9 hours, the same time required for ejaculated spermatozoa (Lee, et al., 1986, supra). Therefore, it appears that a short term exposure to seminal plasma, similar to that which occurs in vivo, dramatically alters the kinetics of the development of spontaneous acrosome reactions.

There is also evidence that epididymal spermatozoa incubated with GAGs and acrosome reaction inducing zona pellucida proteins will not undergo acrosome reactions. Florman, H. N. and N. L. First, 1988b, supra. Thus, rather than allowing the acrosome reaction to spontaneously occur if the zona pellucida protein is used, which would likely induce physiological acrosome reactions, the epididymal spermatozoa do not respond, but the ejaculated spermatozoa do. Therefore, seminal plasma is required.

The GAGs heparin, chondroitin sulfates A, B, or C, and hyaluronic acid all promote the occurrence of acrosome reactions in bovine sperm. The potencies are related to the degree of sulfation of the GAGs. See Handrow, R. P., et al. (1982), "Structural Comparisons Among Glycosaminoglycans to Promote an Acrosome Reaction in Bovine Spermatozoa," *Biochem. Biophys. Res. Comm.*, 107:1326–1332.

Heparin, the most highly sulfated GAG, is also the most potent at stimulating the acrosome reaction in bovine epididymal sperm. Heparin is structurally similar to GAGs in oviductal fluid which act during the capacitation phase of bovine sperm (First, N. L., and J. J. Parrish, 1987, "In-Vitro Fertilization of Ruminants," *J. Reprod. Fert.*, 34(Suppl):151–165; Parrish, et al., 1988a, "Capacitation of Bovine Sperm by Heparin is Correlated with $^3$H-heparin Binding and is Blocked by Protamine Sulfate," *Biol. Reprod.*, 38(Suppl 1):59; Parrish, et al., 1988b, "Capacitation of Bovine Sperm by Heparin," *Biol Reprod.*, 38:1171–1180; Florman, H. M. and N. L. First 1988a, Regulation of Acrosomal Exocytosis. I. Sperm Capacitation is Required for the Induction of Acrosome Reactions by the Bovine Zona Pellucida in Vitro," *Dev. Biol.*, 128:453–463; Parrish, et al., 1989, "Capacitation of Bovine Spermatozoa by Oviduct Fluid," *Biol Reprod.*, In Press), Heparin has been shown to facilitate the acrosomal reaction in bull cauda epididymal (Handrow, et al., 1982, supra) and ejaculated sperm as well as rabbit sperm (Lenz, et al., 1983b, supra). Heparin binds to bull, rabbit and monkey sperm in a saturable, reversible, temperature-, pH-, and $Ca^{2+}$-dependent fashion (Handrow, et al., 1984, "Specific Binding of the Glycosaminoglycan $^3$H-heparin to Bull, Monkey, and Rabbit Spermatozoa In Vitro," *J. Androl.*, 5:51–63). Epididymal and ejaculated sperm cells differ in heparin-binding ability primarily because epididymal sperm cells contain fewer binding sites on them. However, when seminal plasma is added, the number of heparin-binding sites is increased (Lee et al., 1986, supra).

To investigate further the difference in heparin-binding between washed ejaculated and epididymal spermatozoa, Lavin, C. A., et al. (1986, "Characterization of Heparin-Binding Domain From Monkey and Bull Spermatozoa," Paper Presented at The American Fertility Society/Canadian Fertility and Andrology Society Annual Meeting, Abstr.) extracted plasma membranes and outer acrosomal membranes of ejaculated and epididymal spermatozoa. Heparin-binding proteins in those extracts were separated using heparin-sepharose affinity chromatography. More total heparin-binding protein was extracted from ejaculated than epididymal spermatozoa. It was concluded that during ejaculation, heparin-binding proteins were added to or modified on epididymal spermatozoa. This process is presented in schematic form in FIG. 2, which illustrates the heparin-binding sites between ejaculated sperm, i.e., sperm which have been exposed to seminal plasma, and epididymal sperm which have not been exposed to seminal plasma. The first drawing is of an epididymal sperm cell with heparin-binding proteins (colored bowties). The second or middle drawing is of a sperm cell after seminal plasma has been added. After the seminal plasma has been added to the sperm cell, it is believed that the seminal plasma proteins bind to epididymal sperm creating more binding sites for heparin when it is added. When the seminal plasma proteins are added, the epididymal sperm acts similarly to an ejaculated sperm, and the acrosomal reaction, induced by GAGs, takes place faster. If the zona pellucida proteins are added, then seminal plasma exposure is required for the induction of the acrosome reaction. Because the heparin-binding proteins are added to the sperm membranes at ejaculation, the most likely source of the heparin-binding proteins added to the epididymal spermatozoa at ejaculation is the seminal plasma.

The binding of heparin to sperm was found to be related to the conception rate of cows artificially inseminated with those sperm. (Ax, R. L. and R. W. Lenz, 1987, "Glycosaminoglycans as Probes to Monitor Differences in Fertility of Bulls," *J. Dairy Sci.*, 70:1477; U.S. Pat. No. 4,767,703 to Ax, et al.). The relative fertility of bulls, as evaluated by non-return rate, relates to the interaction of GAGs with their spermatozoa.

Since fertility of bulls corresponds to the effectiveness of GAGs to capacitate spermatozoa in vitro and also correlates to the binding affinity spermatozoa possess for heparin, seminal plasma heparin-binding proteins may be important for successful fertilization.

SUMMARY OF THE INVENTION

It is therefore an object of the present invention to isolate and identify substantially pure classes of proteins in seminal plasma which bind to GAGs, and specifically heparin. The term "class or classes of proteins" is meant to indicate one or more proteins from each of classes B1–B5 as presented in the table on page 12 infra. The classes of heparin-binding proteins may be separately identified by a number of characteristics, such as affinity binding, molecular weight and isoelectric point.

It is another object of the invention to distinguish peripheral membrane heparin-binding proteins from integral membrane proteins in plasma membranes of sperm cells. As used herein, the term "peripheral membrane proteins" includes proteins located on the outer surface of the plasma membrane. These proteins may be either intrinsic, i.e., already present on the sperm cell membrane, or extrinsic, i.e., added to the sperm cell membrane from another source such as seminal plasma. Peripheral membrane proteins may be removed by washing with salt. On the other hand, "integral membrane proteins" extend into the membrane lipid bilayer. As such, they are more solidly anchored to the membrane and cannot be removed by sodium chloride. As will be described hereinafter, distinguishing these two types of proteins may be useful as a fertility indicator.

It is still another object of the present invention to detect heparin-binding proteins originating from seminal plasma, which are located on the surface of ejaculated sperm cells, and to distinguish them from intrinsic sperm proteins.

It is further an object of the present invention to isolate, purify and reintroduce heparin-binding proteins from a donor seminal plasma to a recipient seminal plasma. As will be described hereinafter, the ability to isolate, purify and reintroduce the proteins will be useful as a fertility enhancer.

It is still another object of the invention to provide for the synthesis of a bioreagent for antibody assays, which will be useful in a test kit for, for example, a fertility indicator.

These objects and others are met by the present invention which is directed to a method of isolating substantially pure classes of heparin-binding proteins from seminal plasma by treating the seminal plasma, which contains heparin-binding proteins, using affinity chromatography employing heparin moieties linked to an insoluble support matrix to bind the heparin-binding proteins to the matrix. The bound protein is then eluted with an increasing gradient of a substance having a higher affinity to the matrix than the bound protein or a denaturant to remove the bound protein from the matrix. Liquid fractions containing the substantially purified heparin-binding protein components are then collected.

The present invention is also directed to a method of isolating, purifying and reintroducing seminal plasma heparin-binding proteins. This method includes the aforementioned steps as well as isolating and characterizing the substantially purified class of heparin-binding proteins collected from the affinity columns, and adding the substantially purified proteins to the seminal plasma of a recipient.

The present invention is further directed to a method of characterizing seminal plasma in males, comprising treating seminal plasma, which contains heparin-binding proteins, using affinity chromatography employing heparin moieties linked to an insoluble support matrix to bind the heparin-binding proteins to the matrix, eluting the bound protein with an increasing gradient of substance having a higher affinity to the matrix or denaturant than the bound protein to remove the bound protein from the matrix, collecting liquid fractions containing substantially purified heparin-binding proteins, isolating and characterizing the substantially purified proteins, and comparing these isolated and characterized proteins with heparin-binding proteins of a control male with known fertility characteristics.

The present invention is also directed to a method of identifying reversibly adsorbed heparin-binding proteins from intrinsic proteins in the plasma membrane of sperm cells. This method includes the steps of isolating sperm cells from seminal plasma, removing plasma membrane from the sperm cells, forming a purified preparation of the plasma membrane, separating the adsorbed heparin-binding proteins from intrinsic proteins from the plasma membrane, and comparing these plasma membranes with a comparative study wherein the adsorbed proteins have been removed from the surface of the plasma membrane.

The present invention is also directed to a method of synthesizing a bioreagent for an antibody assay to heparin-binding proteins in seminal plasma. The steps include providing seminal plasma containing heparin-binding proteins, treating the seminal plasma using affinity chromatography, eluting the bound protein by gradient elution, and collecting the reagent consisting of liquid fractions containing substantially purified heparin-binding proteins.

The present invention is also directed to the use of radioiodinated seminal plasma heparin-binding proteins in a sperm binding assay.

The present invention is further directed to a method of enhancing the acrosomal reaction in sperm cells. This method includes adding a substantially pure heparin-binding protein to semen which may be deficient in the protein. The heparin-binding proteins have a select set of characteristics, including molecular weights between 14–16 kilodaltons (kD), 24 kDs and 30–35 kDs.

The present invention is also directed to a substantially pure heparin-binding protein composition found in seminal plasma.

Further, the present invention is directed to a bioreagent for antibody assays comprising heparin-binding proteins having a select set of characteristics.

Other objects, features and advantages of the present invention will be apparent from the following detailed description taken in conjunction with the accompanying drawings.

BRIEF DESCRIPTION OF THE DRAWINGS

FIGS. 12a and 12b are 2D SDS-PAGE gels characterizing the type of binding of seminal plasma proteins to epididymal sperm as described in Example 9.

DETAILED DESCRIPTION OF THE INVENTION

Isolation and Purification of Heparin-Binding Seminal Plasma Proteins

The present invention provides a process of isolating and purifying seminal plasma protein components to obtain a protein capable of inducing an acrosomal reaction in a sperm cell. The basic premise behind this invention is the ability of certain proteins in seminal plasma to bind to GAGs and the relation of the proteins to the capacitation, acrosome reaction and fertility of spermatozoa. Although the present invention is directed to GAGs in general such as, for example, heparin, chondroitin sulfates A, B, or C and hyaluronic acid, heparin will be emphasized herein as it is the most highly sulfated and the most potent GAG at stimulating capacitation and the acrosome reaction.

After it was determined that there were heparin-binding proteins in seminal plasma, the next step was to purify the seminal plasma proteins which bound heparin. The protein purification process of choice utilizes affinity chromatography. The principle behind affinity chromatography is the immobilization of a ligand on a stationary support, such as agarose, while maintaining the ability of the ligand to bind other components. The sample to be purified may then be applied to a column containing the immobilized ligand. The material that does not bind to the ligand is washed out in the mobile phase while the material that does bind will still remain in the column bound to the stationary phase. The specifically adsorbed material can be eluted by pH gradient elution techniques or by adding an excess of competing ligand, salts or denaturants which favors dissociation of the material from the ligand according to methods known to the art. The specificity of the purification step is dependent upon the specificity of the ligand and the specificity of the remainder of the stationary phase.

Figure 1:
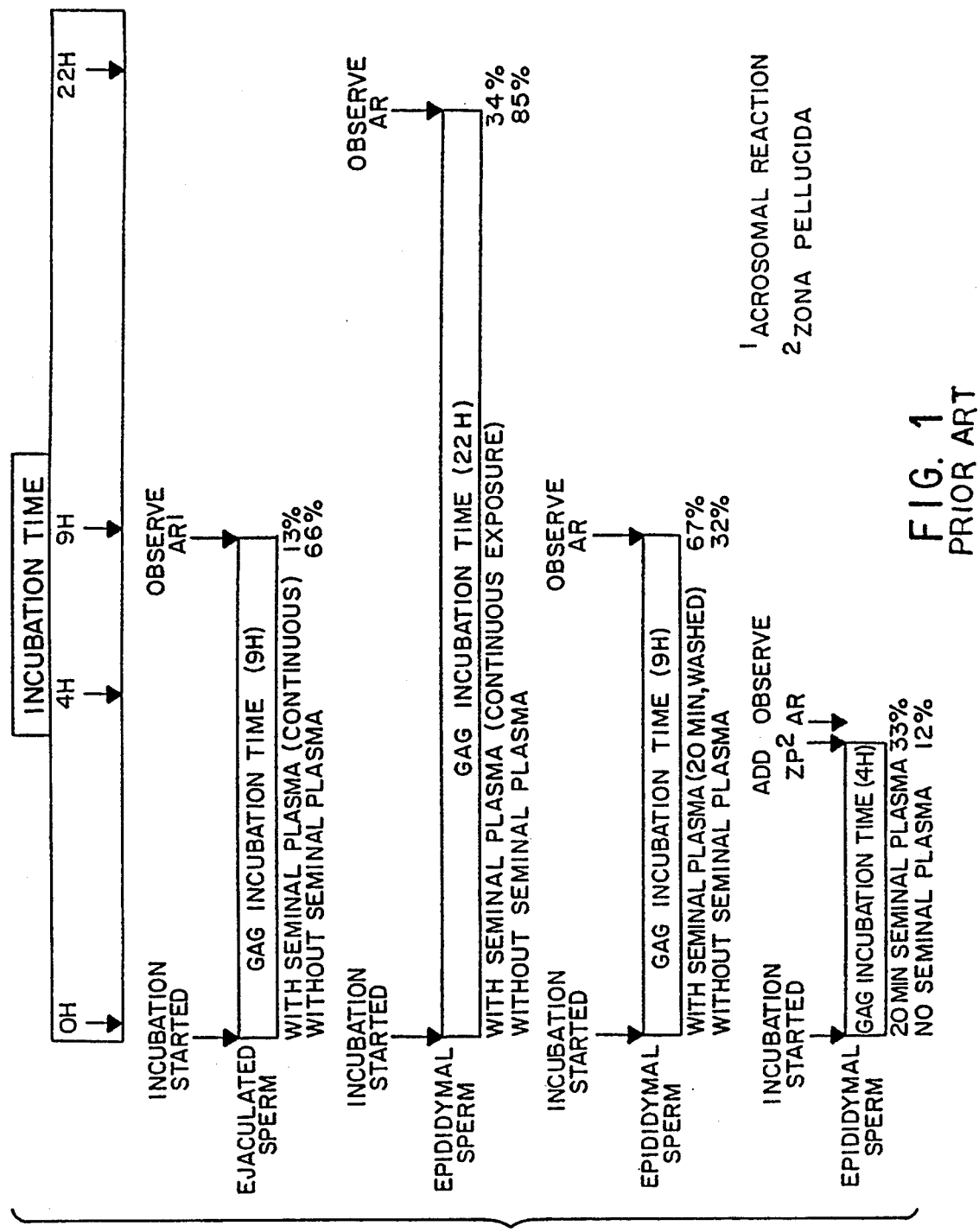
FIG. 1 is a bar graph illustrating the prior art results of several experiments on the kinetics of capacitation and acrosome reactions of epididymal and ejaculated spermatozoa.
Figure 2:
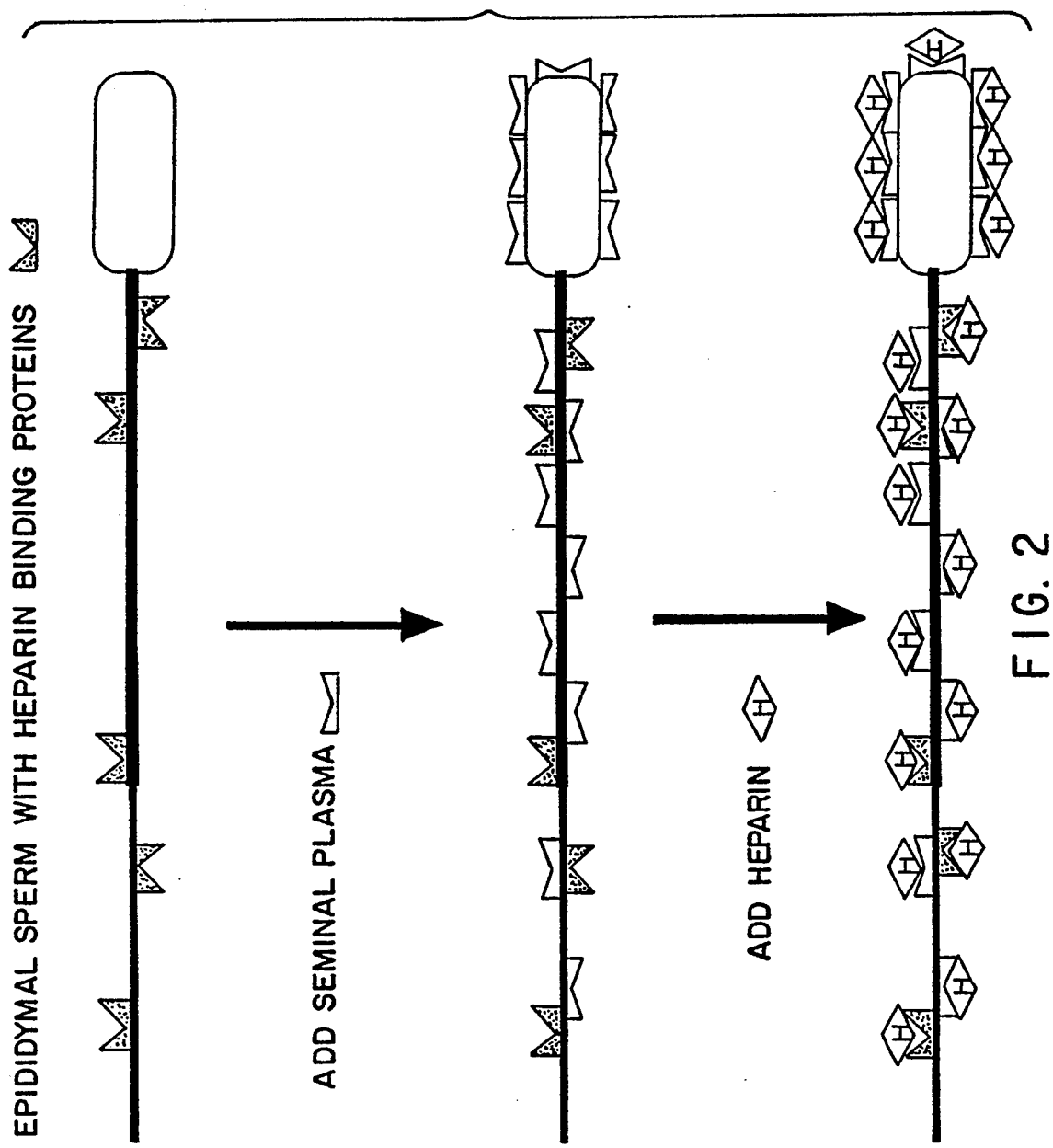
FIG. 2 is a schematic illustration of the difference between the heparin-binding sites of ejaculated spermatozoa and epididymal spermatozoa.
Figure 3:
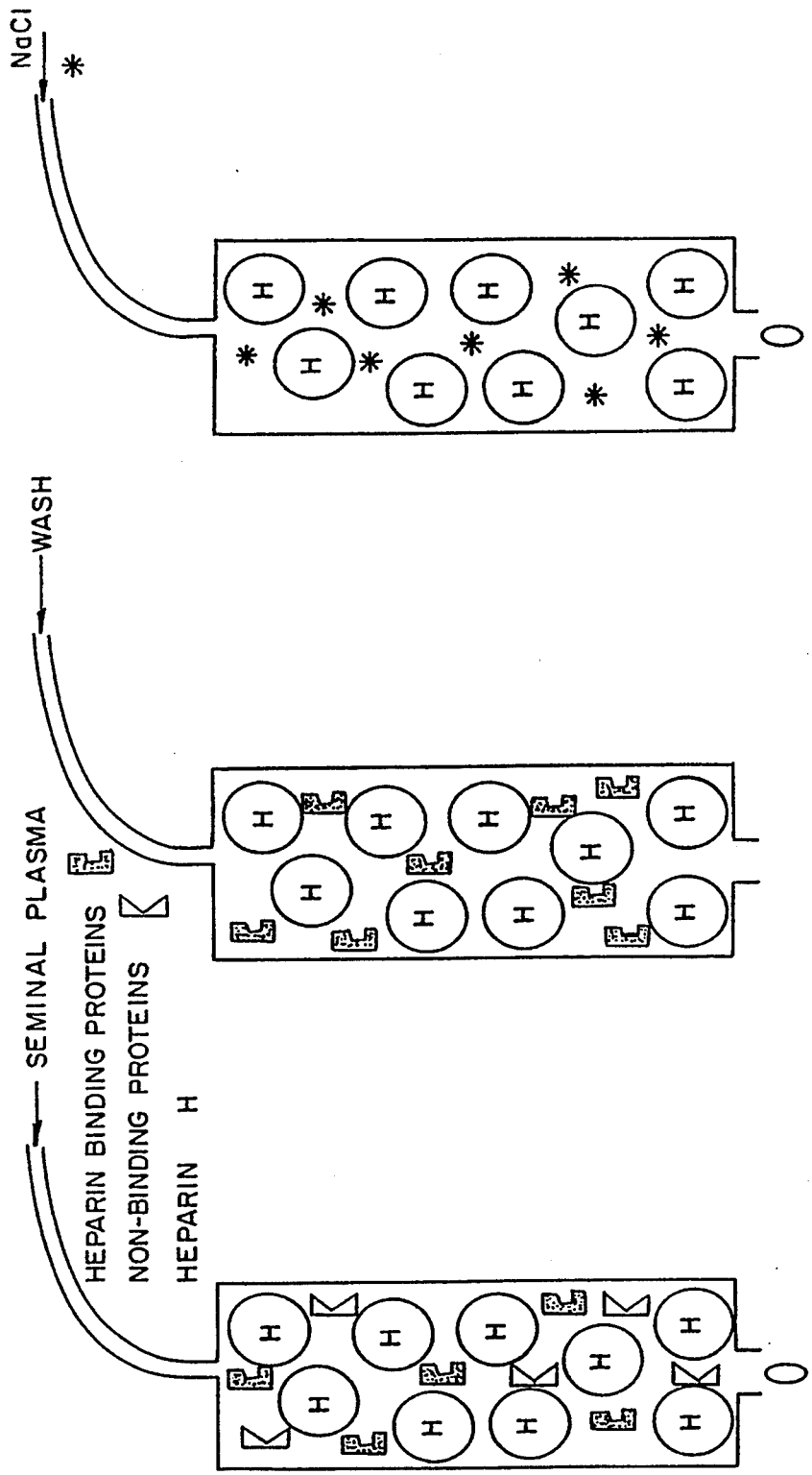
FIG. 3A–3C are schematic illustrations of the affinity chromatography process.

Reference is now made to FIG. 3, which illustrates in schematic form, the affinity chromatography process. In FIG. 3A, seminal plasma comprising heparin-binding proteins (colored bowties) and non-binding proteins (clear bowties) are added to a column containing heparin as the immobilized ligand. As illustrated in FIG. 3B, the non-binding proteins are washed off, leaving the heparin-binding proteins bound to the ligand in the column. As illustrated in FIG. 3C, the bound proteins are then eluted off with an increasing gradient of salt. The resulting liquid fraction includes heparin-binding proteins which have been isolated and purified according to the affinity of the protein to the column.

The examples which follow illustrate two types of affinity chromatography: 1) low pressure liquid chromatography (LPLC) and 2) high pressure liquid chromatography (HPLC). Low pressure liquid chromatography utilizes heparin-sepharose affinity chromatography. Reference is made to Farooqui, A. A. and Horrocks, L. A. (1984), "Heparin-Sepharose Affinity Chromatography," In *Advances in Chromatography*, Vol. 23, Gidding, J. C., ed., Marcel Decker, N.Y. and Lobb, R. R., et al. (1986), "Purification of Heparin-Binding Growth Factors,"*Anal. Biochem.*, 154, pp. 1-14, for a description of this protein purification process. Although useful, LPLC is relatively slow and resolution can be limited if several macromolecules bind with similar affinities to the stationary phase. Thus, the adaptation of affinity chromatography with low pressure systems to a procedure using HPLC has a number of advantages, including increased speed and resolution. It will be seen in the examples that while the seminal plasma proteins were fractionated into 3 binding peaks with LPLC, 7 peaks were resolved using HPLC. Further, the run time was reduced from 18 hours to 2 hours.

Description of the Seminal Plasma Proteins

The examples which follow show that seminal plasma proteins, including those with affinity for heparin, bind to epididymal sperm and regulate the response to heparin. Specifically, the plasma membranes of ejaculated sperm contain a group of 15-17 kD proteins which bound to heparin and are not found on cauda epididymal sperm. Following exposure of epididymal sperm to seminal plasma, the 15-17 kD proteins were present on the cell membranes. The 15-17 kD proteins were the major seminal plasma proteins added to sperm at ejaculation. Other heparin-binding proteins found on both ejaculated and epididymal sperm plasma membrane had molecular weights of 24, 31, and 35 kD and three proteins from 70-100 kD.

The seminal plasma heparin-binding proteins are capable of enabling heparin to capacitate sperm, rendering them responsive to the zona pellucida of the ovum. As illustrated mainly in Example 3, there are specifically five different heparin-binding seminal plasma protein compositions having the following properties:

| Class of Protein | Molecular Weight (Kd) | Molarity of NaCl Required For Elution[1] | Isoelectric Point |
|---|---|---|---|
| B1 | 13, 14–16, 24, 30–35 | 0.15 | 6.5–7.5[2], 4.1–8.0[3], 6–8[4], 5–6.5[5] |
| B2 | 14–16, 24, 30–35 | 0.54 | 4.1–8.0[3], 6–8[4] 5–6.5[5] |
| B3 | 14–16, 24, 30–35 | 0.66 | 4.1–8.0[3], 6–8[4] 5–6.5[5] |
| B4 | 14–16, 24, 31 | 0.74 | 4.1–5.1[3], 6–8[4] 5–6.5[5] |
| B5 | 14–16, 24, 31 | 0.90 | 4.1–5.1[3], 6–8[4] 5–6.5[5] |

[1][NaCl] in M at Peak Apex: Absorbance at 280 nm was monitored to detect protein and conductivity was monitored to detect [NaCl] [See Table 1, infra.]
[2]Mol. wt. = 13
[3]Mol. wt. = 14–16
[4]Mol. wt. = 24
[5]Mol. wt. = 30–35

Each class of proteins purified by affinity chromatography has been determined to induce acrosomal reactions in spermatozoa. Combining all of the classes of proteins together and adding them to epididymal sperm cells results in a degree of acrosomal reaction similar to that expected with normal seminal plasma. Thus, one or a combination of classes of proteins may be significant as a fertility enhancer.

By the addition of one or more of these purified classes of heparin-binding proteins from seminal plasma to the semen of a low fertility male, additional heparin-binding sites may be added to the spermatozoa of low fertility males thus increasing the chances of acrosomal reaction, leading to capacitation and increased fertility.

It has also been determined that the seminal plasma heparin-binding proteins are reversibly adsorbed onto the surfaces of the ejaculated sperm. The adsorbed proteins are believed to be the major proteins in the seminal plasma responsible for inducing capacitation and subsequent acrosomal reaction in response to heparin and fertilization of this spermatozoa. The identification and the isolation of the specific classes of heparin-binding seminal plasma proteins have a number of potential benefits.

Because the heparin-binding ability of the proteins in the seminal plasma is related to capacitation, acrosome reaction and the subsequent fertilization of spermatozoa, the identification and isolation of the proteins in the seminal plasma which bind to heparin has potential benefits in characterizing seminal plasma in males, e.g., low-fertility males, as a fertility enhancer or inhibitor, and in the production of a bioreagent and test kit for determining the fertility of a male.

In the experiments referred to below, the classes of heparin-binding proteins which are reversibly adsorbed onto the plasma membrane of spermatozoa can be readily distinguished from proteins which are integral with the plasma membrane of the spermatozoa. The reversibly-adsorbed or extrinsic proteins are known to originate in the seminal plasma of the male. A comparison of the quality and quantity of the reversibly-adsorbed proteins from a test male in comparison with a male of proven fertility can be useful as a fertility indicator.

In the experiments referred to below, it will be seen that it is possible to isolate, purify and reintroduce active seminal plasma heparin-binding proteins to sperm from a different donor. By the addition of isolated and purified seminal plasma heparin-binding proteins to a male of proven low fertility, the protein component which has the ability to convey the acrosome reaction to the spermatozoa may be useful in enhancing the acrosomal reaction, capacitation and subsequent fertility of the spermatozoa in the seminal plasma of the low fertility male.

The present invention is also directed to the use of radioiodinated seminal plasma heparin-binding proteins (HBP) directly in a sperm binding assay. The proteins are purified preferably by heparin-affinity HPLC, radiolabeled such as by radioiodination and placed in a filtration assay similar to the $^3$H-heparin binding assay. By this process, it will be possible to determine whether ejaculated sperm from infertile males are "HBP-deficient" or "HBP-saturated" without resorting to antibodies against the proteins. This process is also useful for detecting defects in sperm membranes, i.e., an inability to bind seminal plasma HBPs, in unexplained cases of infertility where such proteins are present in the seminal plasma and sperm characteristics are otherwise normal.

The heparin-binding protein compositions can also be isolated as bioreagents and used to prepare polyclonal and monoclonal antibodies for detection of fertility characteristics in males and to follow a course of treatment. The antibodies can be provided in test kits which are used to diagnose clinically suspected reduced fertility in males and various clinical settings. The protein can be recognized and distinguished from other proteins according to the characteristics determined in the experiments below.

Antibodies can be prepared according to methods known to the art. For example, seminal plasma proteins can be employed to produce monoclonal antibodies to seminal plasma proteins utilizing the procedure described by Fazekus, et al. (1980), *J. Immunol. Methods*, 35:1. The essential steps are as follows:

1) immunize an animal, preferably a rodent such as a rat or mouse, with seminal plasma protein;

2) isolate B-lymphocytes, suitably spleen lymphocytes, from the immunized animal;

3) re-fuse the isolated B-lymphocytes with myeloma cells from an animal, preferably a rodent such as a rat or mouse;

4) select from the fused cells those hybridoma cell lines which react positively with seminal plasma proteins; and 5) clone the hybridoma cells to produce additional monoclonal antibodies.

Procedures for performing each of these steps are well known to those skilled in the art.

Any of a large number of clinical tests may be, employed utilizing the antibodies of this invention. Typical tests include radioimmunoassay, enzyme-linked-immunoassay, precipitation, agglutination, direct and indirect immunofluorescence and complement fixation. These test kits may employ competitive and sandwich-type assays.

A wide variety of test kits are possible to take advantage of the advances in the diagnostic arts made possible by this invention.

The examples below provide specific examples of the invention disclosed herein, although the invention is not to be understood as limited in any way to the terms and scope of the examples.

EXAMPLE 1

Comparison of Heparin-Binding Protein Compositions in Plasma Membranes from Epididymal and Ejaculated Bovine Spermatozoa by 1-Dimensional Sodium Dodecylsulfate-Polyacrylamide Gel Electrophoresis (1D SDS-PAGE)

Proteins from purified plasma membranes were compared according to the following manner:

Plasma Membrane Isolation

Bovine ejaculated spermatozoa were collected using an artificial vagina. Caudae epididymides were incised and spermatozoa were obtained by retrograde flushing through the vas deferens with TALP (100 mM NaCl, 3.1 mM KCl, 1.5 mM $MgCl_2$, 2 mM $CaCl_2$, 0.3 mM $NaH_2PO_4$, 25 mM $NaHCO_3$, 10 mM HEPES, 1 mM Na Pyruvate, 21.6 mM lactate, 6 mg/ml BSA (essentially fatty acid free, Sigma Chemical Co., St. Louis, Mo.), 100 units/ml penicillin, 100 ug/ml streptomycin, pH 7.4. Ejaculated and epididymal cells were centrifuged at 300 g for 10 minutes and the epididymal sperm were resuspended to $2 \times 10^9$ cells/ml. in TALP. An equal volume of seminal plasma was added to the epididymal sperm (which is similar to the seminal plasma volume/sperm cell ratio of bovine semen) and the sample was mixed end-over-end at 22° C. for 20 minutes. All subsequent steps were carried out at 4° C. Cells were centrifuged for 10 minutes at 300 g and the pellet was suspended in 5 ml of isolation buffer (40 mM Tris, 250 mM sucrose, 2 mM EDTA, 5 mM benzamidine, 1 mM PMSF, 1 uM pepstatin, 1 uM leupeptin and 0.01% azide pH 7.35). Cells were separated from noncellular debris by centrifugation though a Percoll cushion (isolation buffer: Percoll [Sigma Chem. Co., St. Louis, Mo.]:2.5M sucrose, 5.9:3.7:0.4) at 800 g for 15 minutes and the resulting pellet was washed once (300 g) to remove excess Percoll. Cells were resuspended in 5 ml of isolation buffer and disrupted by nitrogen cavitation in a Parr bomb (Parr Instrument Co., Moline, Ill.) using 600 psi of nitrogen for 10 minutes according to the process described in Noland, et al., 1983, "Purification and Partial Characterization of Plasma Membranes from Bovine spermatozoa," *Biol. Reprod.*, 29:987–998; and Winer and Ax, 1988, "Heparin Binding Proteins in Purified Plasma Membranes of Ejaculated Bovine Spermatozoa," *44th Ann. Mtg. Amer. Fert. Soc.*, (abstr. 0–66).

Following release of the pressure, the cavitated cells were centrifuged at 1000 g for 10 minutes, the supernatant was decanted and the pellet resuspended in isolation buffer. The pellet was washed twice with isolation buffer and the pooled supernatants were adjusted to a final volume of 13.5 ml with isolation buffer. Percoll (5.9 ml) and 0.6 ml of 2.5M sucrose were added and the suspension was centrifuged for 30 minutes at 34,000 $g_{ave}$. The uppermost band resolved by the self-generating Percoll gradient was aspirated, diluted to 20 ml in isolation buffer and washed from the Percoll by centrifugation at 150,000 $g_{ave}$ for 60 minutes. The resulting pellet was washed again in isolation buffer to remove Percoll. The final pellet was resuspended in 50 mM $NH_4HCO_3$, assayed for protein and lyophilized.

The membrane proteins were compared by 1-D SDS-PAGE. Reference is made to Laemmli, 1970, "Cleavage of Structural. Proteins During Assembly of the Head of Bacteriophage T4," *Nature*, 227:680–685.

Samples were solubilized by heating in a boiling water bath for 5 minutes in electrophoresis sample buffer (62.5 mM Tris-HCl, 2% sodium dodecyl sulfate, 10% glycerol, pH 6.8) with or without 5% 2-mercaptoethanol. Samples were separated by 1-dimensional discontinuous gel electrophoresis using a 1 cm. 4% acrylamide stacking gel and a 12.5 cm. 15% acrylamide separating gel (0.75 mm. thick). Phosphorylase b (molecular weight 97,400), BSA (66,200), ovalbumin (42,700), carbonic anhydrase (31,000), soybean trypsin inhibitor (21,500) and lysozyme (14,400) were used as molecular weight markers (BioRad, Richmond, Calif.). After electrophoresis the gels were fixed and silver stained according to the method described in Merril, et al., 1981, "Ultrasensitive Stain for Proteins in Polyacrylamide Gels Shows Regional Variation in Cerebrospinal Fluid," *Science*, 211:1437-1438.

Figure 4:
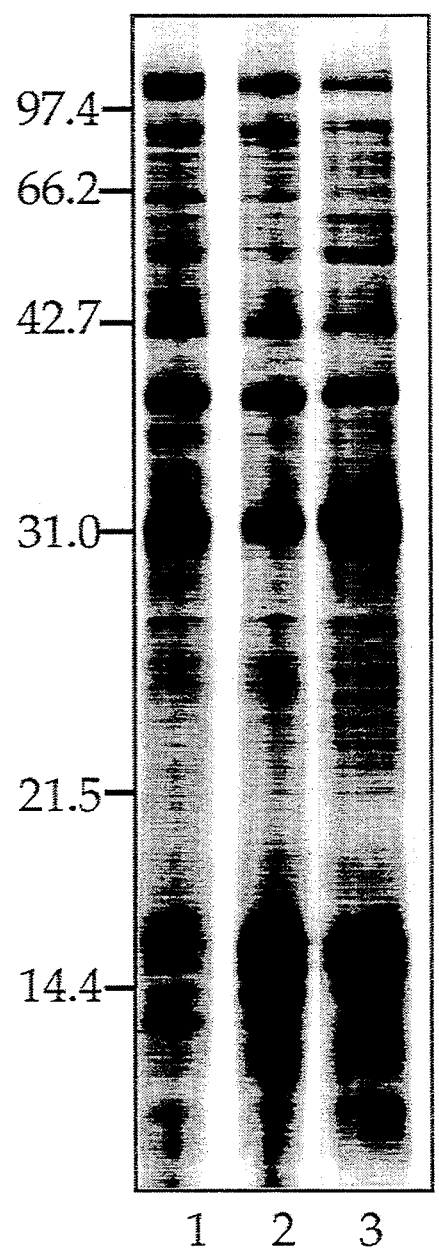
FIG. 4 is a one dimensional sodium-dodecyl sulfate polyacrylamide gel (1D SDS-PAGE) comparing plasma membrane proteins from epididymal sperm, epididymal sperm exposed to seminal plasma and ejaculated sperm.

Reference is now made to FIG. 4 for a comparison of plasma membrane proteins from epididymal sperm, epididymal sperm exposed to seminal plasma and ejaculated sperm by SDS-PAGE. Shown is a representative gel from one of ten separate preparations. In lane 1 are proteins from epididymal sperm plasma membranes; in lane 2 are proteins from plasma membranes from epididymal sperm exposed to seminal plasma; and in lane 3 are proteins from ejaculated sperm plasma membranes. The migration of molecular weight standards is indicated on the left.

The major difference between membranes from epididymal and ejaculated sperm was that ejaculated sperm contained 3 bands at 15, 16 and 17 kD. These proteins were also found in epididymal sperm membranes exposed to seminal plasma in vitro for 20 minutes.

EXAMPLE 2

Comparison of Plasma Membrane Proteins by 2-Dimensional Gel Electrophoresis

Cauda epididymal sperm were exposed for 20 minutes to seminal plasma. Plasma membranes from epididymal sperm or epididymal sperm exposed to seminal plasma were purified as described in Example 1 and prepared for electrophoresis by boiling 5 minutes in a SDS sample buffer (2.3% SDS, 5% 2-mercaptoethanol, 10% glycerol and 60 mM Tris, pH 6.8). Two-dimensional (2-D) gel electrophoresis was performed according to the method of O'Farrel, 1975, "High Resolution Two-Dimensional Electrophoresis of Proteins," *J. Biol. Chem.*, 250:4007–4021, by the Kendrick Laboratory (Madison, Wis.). Thirty micrograms (ug) of protein were applied to the gels. Isoelectric focusing (IEF) using 1.5% pH 5–7, 1.5% pH 5–8 and 1.0% pH 3.5–10 ampholines (LKB Instruments, Baltimore) was carried out for 9600 volt hours (700 volts for 13 hours, 45 minutes). Forty ng of an IEF internal standard, vitamin D-dependent calcium-binding protein, mol. wt. 27,000 and isoelectric point (pI) 5.2 was added to the samples. The final tube gel pH gradient extended from pH 4.1 to pH 8.1 as measured by a surface pH electrode (BioRad, Richmond, Calif.) and colored acetylated cytochome pI markers (Calbiochem-Behring, La Jolla, Calif.) run in an adjacent tube. The following proteins (Sigma Chemical Co., St. Louis, Mo.) were added as molecular weight standards to the agarose which sealed the tube gels to the slab gels: myoin (220,000 Da), phosphorlyase A (94,000 Da), catalase (60,000 Da), actin (43,000 Da) and lysozyme (14,000 Da). These standards appeared as fine horizontal lines on the silver stained (Oakley, et al., 1980, "A Simplified Ultrasensitive Silver Stain for Detecting Proteins in Polyacrylamide Gels," *Anal. Biochem.*, 105:361–363) 10% acrylamide slab gels.

Figure 5A:
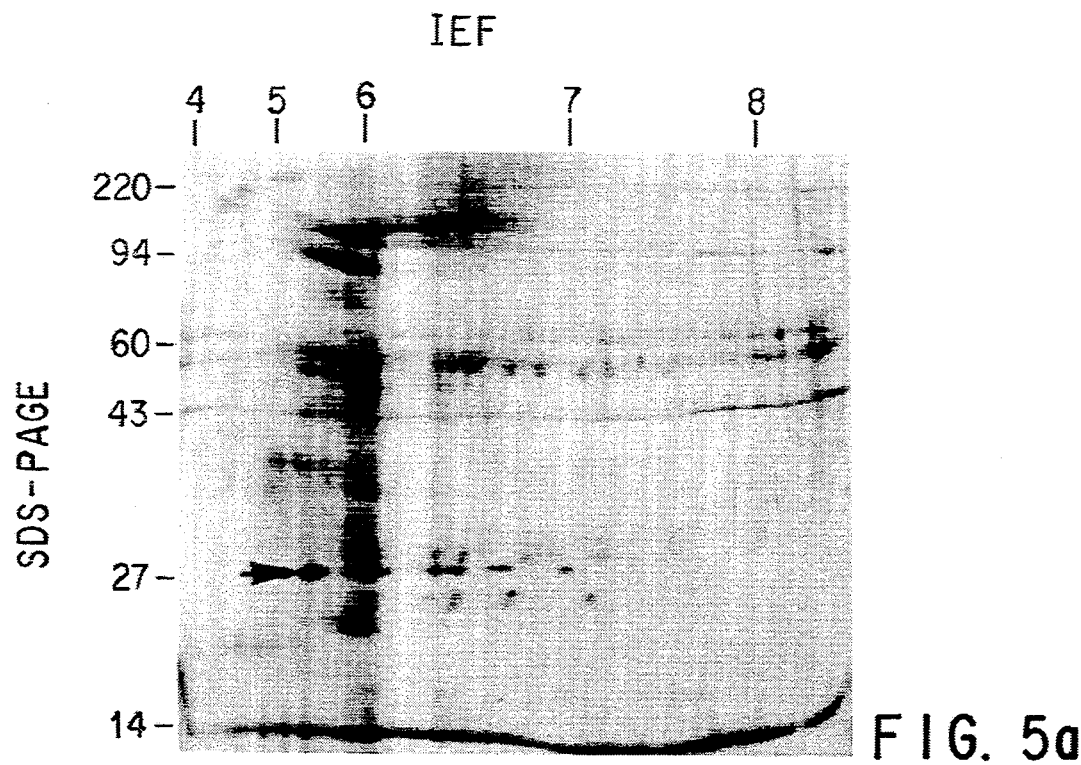
FIGS. 5a and 5b are two dimensional (2D) SDS-PAGE gels comparing the plasma membrane of FIG. 4.
Figure 5B:
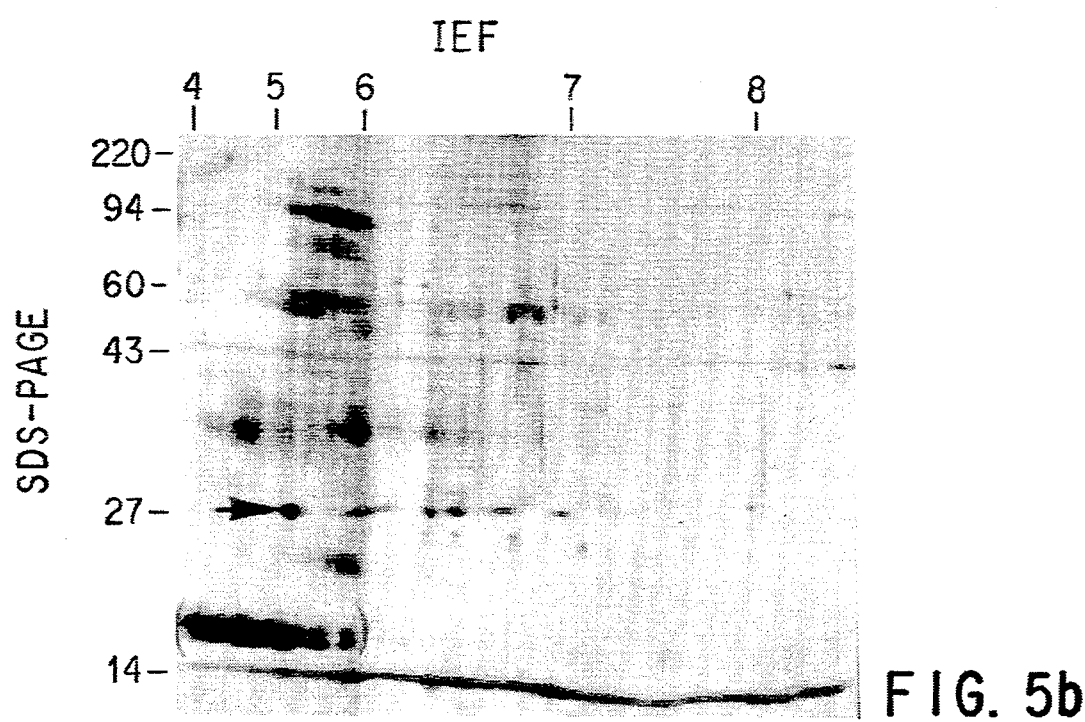

Reference is now made to FIGS. 5a and 5b for a comparison of plasma membrane proteins by 2-dimensional gel electrophoresis. The gel in FIG. 5a is from epididymal sperm and the gel in FIG. 5b is from epididymal sperm exposed to seminal plasma. An internal standard (pI 5.2, mol. wt. 27 kD) was identified with an arrow on the silver-stained gels. The final tube gel pH gradient is shown above the gels and molecular weight markers are shown as horizontal lines. Two-D gel electrophoresis indicated the proteins had a pI range of 4.1 to 5.5. These may be variants of similar proteins with differing glycosylation. Other major proteins were found in both epididymal and ejaculated sperm membranes including proteins migrating as 24 to 28 kD, 31 kD, and many from 35 to 120 kD.

EXAMPLE 3

Comparison of Plasma Membrane Heparin Binding Proteins from Epididymal Sperm, Epididymal Sperm Exposed to Seminal Plasma and Ejaculated Sperm by Western Blotting Plasma membranes were isolated from ejaculated sperm, non-exposed cauda epididymal sperm and cauda epididymal sperm exposed for 20 minutes to seminal plasma. Membrane proteins (50 ug protein) from each preparation of cells were loaded for SDS-PAGE. After electrophoresis the proteins were electro-transferred to nitrocellulose (0.2 um pore size, Schleicher and Schuell, Keene, N.H.) for 2 hours at 30 V and then 2 hours at 60 V according to methods described in Towbin, et al., 1979, "Electrophoretic Transfer of Proteins from Polyacrylamide Gels to Nitrocellulose Sheets: Procedures and Some Applications," *Proc. Natl. Acad. Sci. USA*, 76:4350–4354; and Burnett, 1981, "Western Blotting: Electrophoretic Transfer of Proteins from Sodium Dodecyl Sulfate-Polyacrylamide Gels to Unmodified Nitrocellulose and Radiographic Detection with Antibody and Radioiodinated Protein A," *Anal. Biochem.*, 112: 195–203, in transfer buffer (25 mM Tris, 192 mM glycine, 20% methanol, pH 8.3). The nitrocellulose blot was blocked with 3% BSA and incubated in labeling buffer (40 mM Tris, 2 mM $CaCl_2$, 0.05% Tween-20, pH 7.35) with 4 ug/ml of [$^{125}$I]-heparin for 3 hours at 22° C. Cardin, et al., 1984, "Visualization of Heparin-Binding Proteins by Ligand Blotting With $^{125}$I-heparin," *Anal Biochem.*, 137:368–373. The unbound [$^{125}$I]-heparin was washed from the blot with 5 changes of labeling buffer (10 minutes each) and the blot was dried. Autoradiography was performed to determine which proteins bound [$^{125}$I]-heparin.

Figure 6:
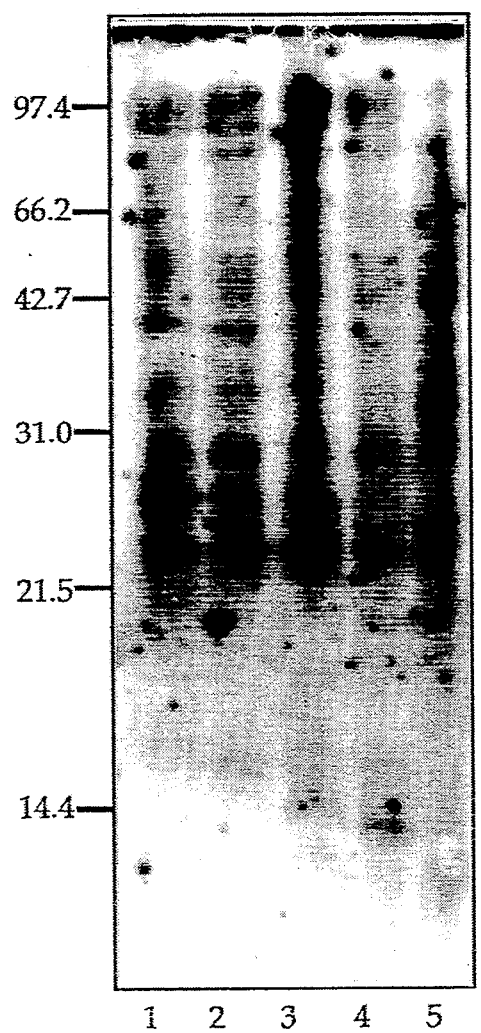
FIG. 6 is an autoradiogram of a western blot comparing plasma membrane heparin-binding proteins from epididymal sperm, epididymal sperm exposed to seminal plasma and ejaculated sperm.

Reference is made to FIG. 6 for a comparison of plasma membrane heparin-binding proteins from epididymal sperm, epididymal sperm exposed to seminal plasma and ejaculated sperm by Western blotting. The autoradiogram is representative of 5 separate membrane preparations. In lanes 1 and 3 the disulfide bonds are left intact (non-reduced). In lanes 2, 4 and 5, a reducing agent has been added to break the disulfide bonds (reduced). Lanes 1 and 2 therefore represent plasma membrane proteins from epididymal sperm under nonreducing and reducing conditions, respectively. Lanes 3 and 4 represent plasma membrane proteins from a mixture of epididymal sperm and seminal plasma under nonreducing and reducing conditions, respectively. Plasma membrane proteins from ejaculated sperm under reducing conditions are represented in lane 5.

Autoradiography detected [$^{125}$I]-heparin labeling of the 15–17 kD membrane proteins of ejaculated sperm and epididymal sperm exposed to seminal plasma, but none in the same molecular weight range in membrane proteins from epididymal sperm. Additional heparin binding proteins were found in membranes from both epididymal and ejaculated sperm with mol. wt. of 24, 31, and 35 kD and 3 between 70 and 100 kD.

EXAMPLE 4

Isolation of Heparin-Binding Proteins by Low Pressure Liquid Affinity Chromatography (LPLC)

Since exposure of epididymal sperm to seminal plasma, in vivo and in vitro, causes addition of the 15, 16 and 17 kD proteins to sperm membranes and 14–17 kD heparin-binding proteins are major components of seminal plasma (Miller, et al., 1987, "Isolation and Characterization of Seminal Fluid Proteins that Bind Heparin. Proc. Regulation of Ovarian and Testicular Function," *Adv. Exp. Med Biol.*, 219:597–601), seminal plasma from vasectomized bulls was fractionated using heparin affinity chromatography.

Heparin, N-desulfated heparin or Tris (used in the derivatization procedure to block residual active groups) were covalently coupled to tresyl-activated Sepharose (Pharmacia, Piscataway, N.J.). Tresyl-Sepharose (2 g.) was swollen in 1 mM HCl and washed for 1 hour on a nylon filter overlying a sintered glass filter. Heparin or N-desulfated heparin (240 mg.), prepared by solvolytic removal of N-sulfate from the pyridinium salt of heparin was dissolved in 10 ml. of coupling buffer (0.1M $NaHCO_3$, 0.5M NaCl, pH 8.3) and mixed with the gel in an end-over-end fashion for 2 hours. Excess heparin was washed from the gel and residual active sites on the gel were blocked by incubation with 0.1M Tris-HCl, pH 8 for 4 hours using end-over-end agitation. A third column was prepared using 2 g. of tresyl-Sepharose blocked with 0.1M Tris. All gels were washed with 3 alternating cycles of 0.1M acetate, 0.5M NaCl, pH 4 and 0.1M Tris-HCl, 0.5M NaCl pH 8.0. The derivatized gels were poured into 1.5×10 cm columns and equilibrated in TC buffer (40 mM Tris, 2 mM $CaCl_2$, 1 mM PMSF, 1 uM pepstatin, 1 uM leupeptin, 0.01% sodium azide, pH 7.35).

Bovine seminal plasma was collected from 3 vasectomized bulls and pooled. Particulates were removed by centrifuging twice for 20 minutes at 1000 g. and once for 20 minutes at 3000 g. The supernatant was stored at $-196°$ C. Seminal plasma supernatant was ultrafiltered on a Stirred Cell (Amicon, Danvers, Mass.) with a YM-5 membrane (5,000 Da cutoff) against TC buffer. The sample (5 mg) was applied to the heparin-Sepharose, N-desulfated heparin-Sepharose and Tris-Sepharose columns and the columns were washed with 30 ml. of TC buffer. A 200 ml. linear 0 to 2M NaCl gradient in TC buffer at a flow rate of 0.3 ml/min. was used to elute the columns. Eluates were monitored for protein by measuring absorbance at 280 nm and for [NaCl] by measuring conductivity.

Figure 7A:
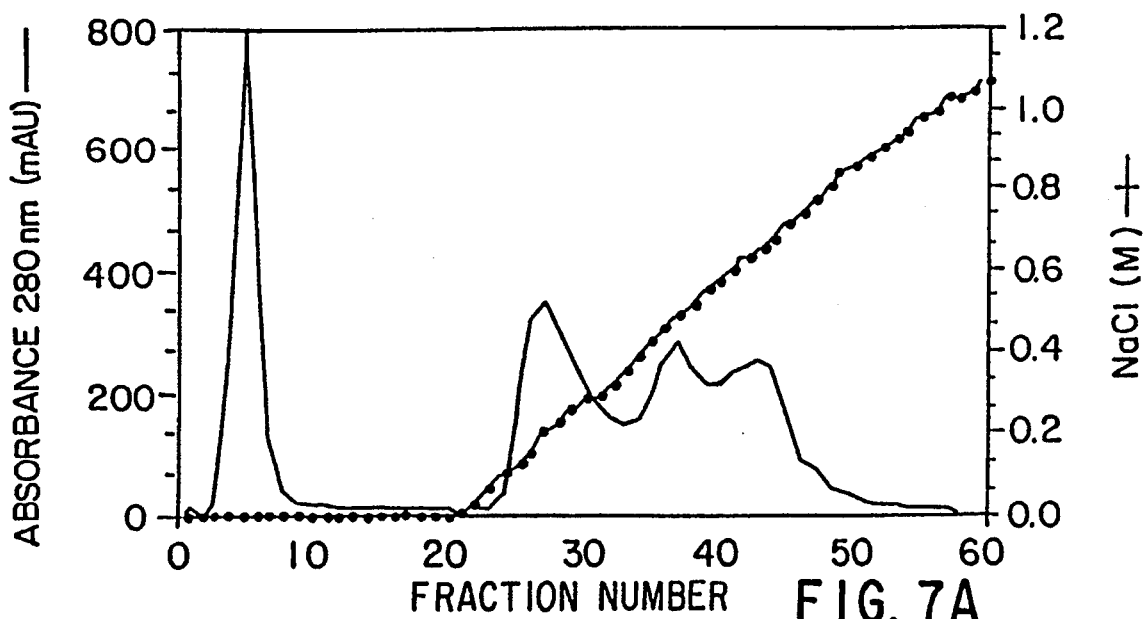
FIGS. 7A–C are graphs illustrating heparin affinity low pressure liquid chromatography (LPLC) separation of seminal plasma heparin-binding proteins.
Figure 7B:
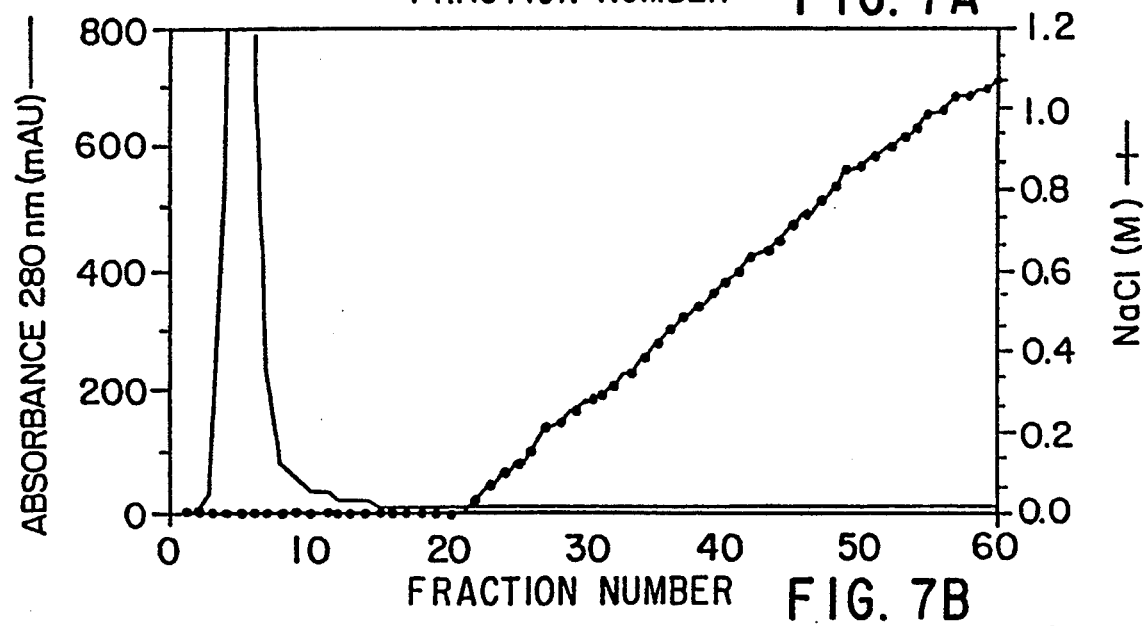
Figure 7C:
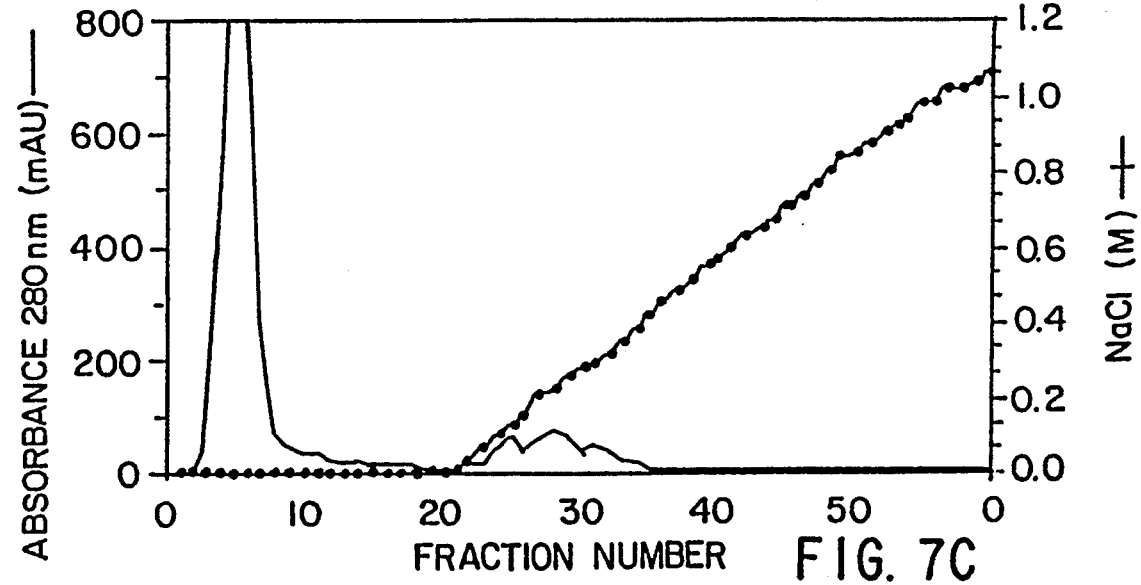

Reference is now made to FIGS. 7A–C for graphs illustrating LPLC separation of seminal plasma heparin-binding proteins. Five mg of seminal plasma protein in TC buffer were loaded onto a heparin-Sepharose (FIG. 7A), a Tris-Sepharose (FIG. 7B) or a N-desulfated heparin-Sepharose (FIG. 7C) column. The columns were washed and then eluted with a 0 to 2M NaCl gradient in TC buffer. Protein was detected by absorbance at 285 nm and NaCl was detected by conductivity. Shown is a representative chromatographic separation which was performed in triplicate.

Fifty percent of the total protein bound to a heparin-Sepharose column eluted as 3 peaks at 0.2, 0.5 and 0.65M NaCl (FIG. 7A). To verify that proteins were binding to the heparin component of the matrix, seminal plasma was applied to a Tris-Sepharose column. No binding of seminal plasma protein was observed to Tris-Sepharose (FIG. 7B). As a further specificity control, seminal plasma was applied to a N-desulfated heparin-Sepharose column, since N-desulfated heparin does not bind to or capacitate sperm (Miller and Ax, 1988, "Chemical N-Desulfation of Heparin Negates its Ability to Capacitate Bovine Spermatozoa," Ann. Mtg. of Amer. Assn. Advancement Sci., (Abstr. A-10)). Approximately 10% of the total seminal plasma protein bound to N-desulfated heparin-Sepharose and all the protein eluted prior to 0.4M NaCl (FIG. 7C). Therefore, the binding to heparin-Sepharose by seminal plasma protein was judged to be specific to native heparin and N-sulfation was important for the binding interaction.

EXAMPLE 5

Isolation of Heparin-Binding Proteins by High Pressure Liquid Affinity Chromatography Bovine seminal plasma was collected according to the method of Example 4. For high pressure liquid chromatography (HPLC), a Pierce (Rockford, Ill.) SelectiSphere-10, tresyl-activated column (25 cm×5 mm) was placed in line and acetone in the column was removed by 200 ml. of water. Another 200 ml. of HPLC-coupling buffer (0.2M $NaH_2PO_4$, 0.5M NaCl, pH 7.5) were used to equilibrated the column to derivatization conditions. A solution of 210 mg. of heparin (Calbiochem, LaJolla, Calif.) in 300 ml. of HPLC-coupling buffer was pumped though the column at 1 ml/min. The column was washed with 200 ml. of HPLC-coupling buffer. To block residual groups, 200 ml. of 0.2M Tris (pH 8.0) were passed through the column.

Approximately 3 mg. of seminal plasma supernatant protein in TC buffer were loaded onto the high performance heparin affinity column. Unbound material was eluted with 20 ml. of TC buffer at 1 ml/min. A linear 90 ml. gradient of 0 to 1.2M NaCl in TC buffer was used to elute bound material. Fractions of 1 ml. were collected throughout the run. Eluted protein was detected by monitoring absorbance at 280 nm and [NaCl] was determined by measuring conductivity.

Figure 8:
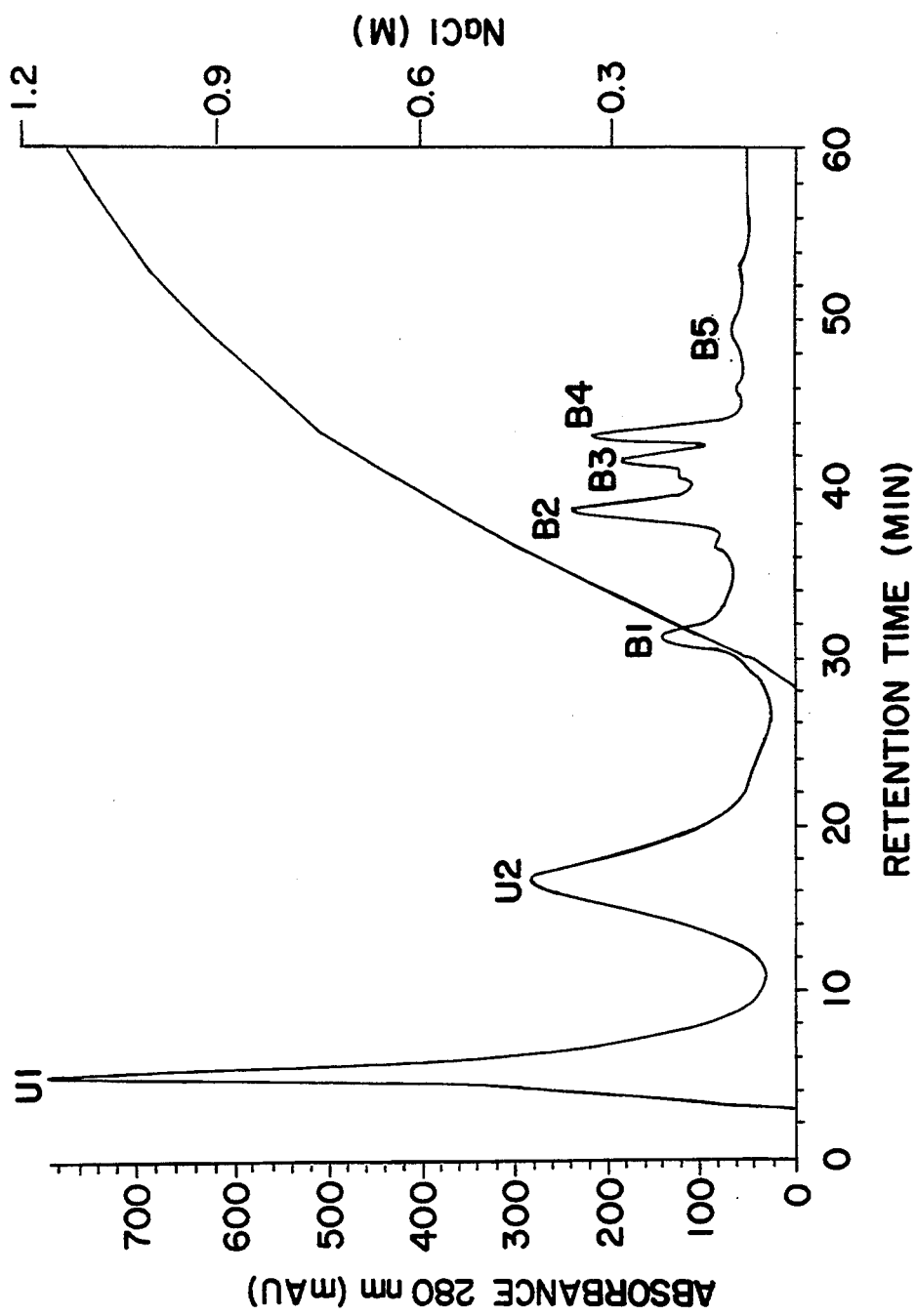
FIG. 8 is a graph illustrating heparin affinity high pressure liquid chromatography (HPLC) separation of seminal plasma heparin binding proteins.

Reference is now made to FIG. 8 which is a graph illustrating the high pressure heparin affinity chromatography separation of seminal plasma heparin-binding proteins. Protein peaks not binding to the column (U1 and U2), as well as those binding to the column (B1–B5) are labeled. A representative chromatogram from 20 separations is shown. The first unbound peak (U1) accounted for 39% of the protein while the second2(U2), accounted for 33% of the total seminal plasma protein. Five heparin-binding peaks were separated, B1, B2,B3, B4, and B5, eluting at NaCl concentrations of 0.15, 0.54, 0.66, 0.74, and 0.90M, respectively. The percentage of total protein in each peak ranged from 1.7 to 9.5%. Separation into 5 peaks in 60 minutes was achieved with the heparin affinity HPLC.

To speed separation and improve resolution, HPLC was employed for heparin affinity separation. Reference is now made to Table 1 for the retention times and amounts of protein peaks separated by heparin affinity HPLC:

TABLE 1

| Peak | Ret. Time at Peak Apex (min)* | [NaCl] in M at Peak Apex** | Protein Pooled Bet. times (min) | % of Total Area Under Each Peak§ |
|---|---|---|---|---|
| U1 | 5.0 | 0 | 2–11 | 39.0 |
| U2 | 16.8 | 0 | 11–26 | 33.2 |
| B1 | 31.3 | 0.15 | 26–35 | 7.5 |
| B2 | 38.7 | 0.54 | 35–40 | 9.5 |
| B3 | 41.7 | 0.66 | 40–43 | 4.7 |
| B4 | 43.2 | 0.74 | 43–46 | 4.4 |
| B5 | 49.3 | 0.90 | 46–60 | 1.7 |

*Seminal plasma (3 mg. protein) was fractionated by heparin affinity heparin affinity HPLC. The proteins binding to the column were eluted with a 0 to 1.2 M NaCl gradient.
**Absorbance at 280 nm was monitored to detect protein and conductivity was monitored to detect [NaCl].
§ The relative proportion of protein in each peak was estimated by integration of peak areas. The specified fractions were pooled, desalted and lyophilized.

EXAMPLE 6

Characterization of Heparin Affinity HPLC Isolates in Seminal Plasma by 1-D and 2-D SDS-PAGE Ten ug of protein from each peak generated in 2Example 5 were dissolved in electrophoresis sample buffer with 5% 2-mercaptoethanol, subjected to SDS-PAGE and silver stained according to the methods described in Example 2.

Figure 9:
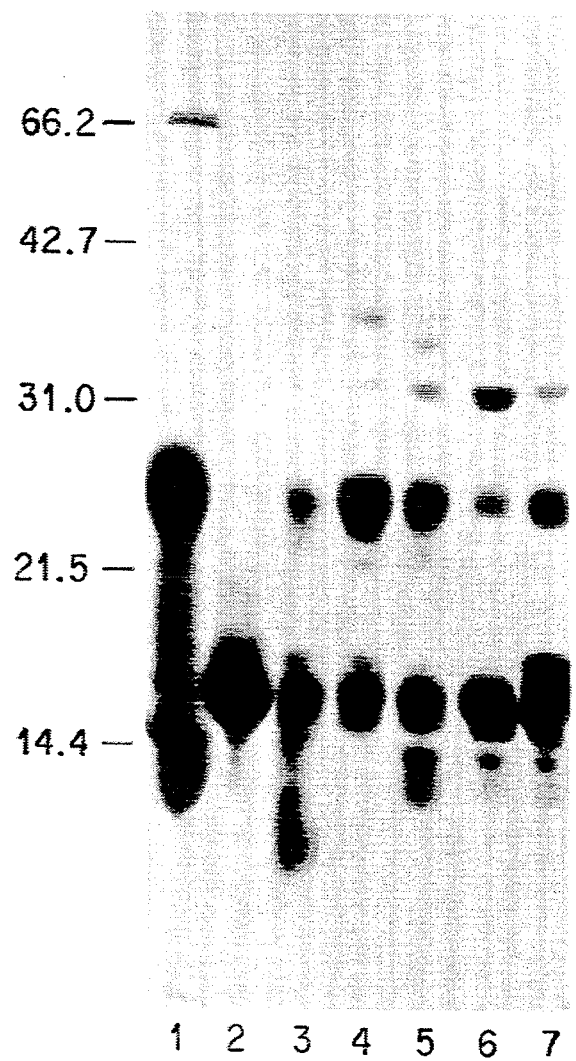
FIG. 9 is a 1D SDS-PAGE gel characterizing the HPLC isolates of Example 5.

Reference is now made to FIG. 9 for a characterization of the molecular weight heparin affinity HPLC isolates. The migrations of molecular weight standards are shown on the left. Lane 1 characterizes peak U1, lane 2 is U2, lane 3 is B1, lane 4 is B2, lane 5 is B3, lane 6 is B4, and lane 7 is B5. The results are typical for the 3 separate preparations assayed.

Peak U1 was composed of 13–18, 24, 66 and 70 kD proteins. Peak U2 contained mainly 14 and 15 kD proteins with multiple isoelectric variants. Proteins with similar molecular weight and isoelectric points were found among several of the heparin-binding peaks (B1–B5). Peak B1 (Lane 3) contained 14–18 kD proteins with a broad. isoelectric distribution. There were also minor 24 kD basic proteins. Peak B2 (Lane 4) contained similar proteins but a greater proportion of the 24 kD basic proteins as well as a minor band at 31 kD. This 31 kD band was more intensely stained in Peak B3 (Lane 5) and B4 (Lane 6), while the 24 kD basic proteins were less intensely stained. Peak B5 contained primarily the acidic 14–18 kD proteins.

EXAMPLE 7

Identification of Seminal Plasma Proteins in Heparin Affinity HPLC Peaks as Heparin-Binding Proteins Because 14–18 kD spots were found in the unbound peaks (U1 and U2) as well as B1–B5, the structural differences necessary for heparin affinity may be very subtle. Alternatively, because heparin affinity chromatography was performed under non-dissociative conditions, the 14–18 kD proteins may have been aggregating to other proteins which bind to the heparin column. To differentiate between these two possibilities, the seminal plasma proteins were separated by SDS-PAGE, transferred to nitrocellulose and incubated with [$^{125}$I]-heparin. Fifty ug of each peak or control proteins were solubilized in SDS electrophoresis buffer containing 5% 2-mercaptoethanol and separated by SDS-PAGE. After electrophoresis the proteins were transferred to nitrocellulose and the blots incubated with 4 ug/ml of [$^{125}$I]-heparin.

Figure 10:
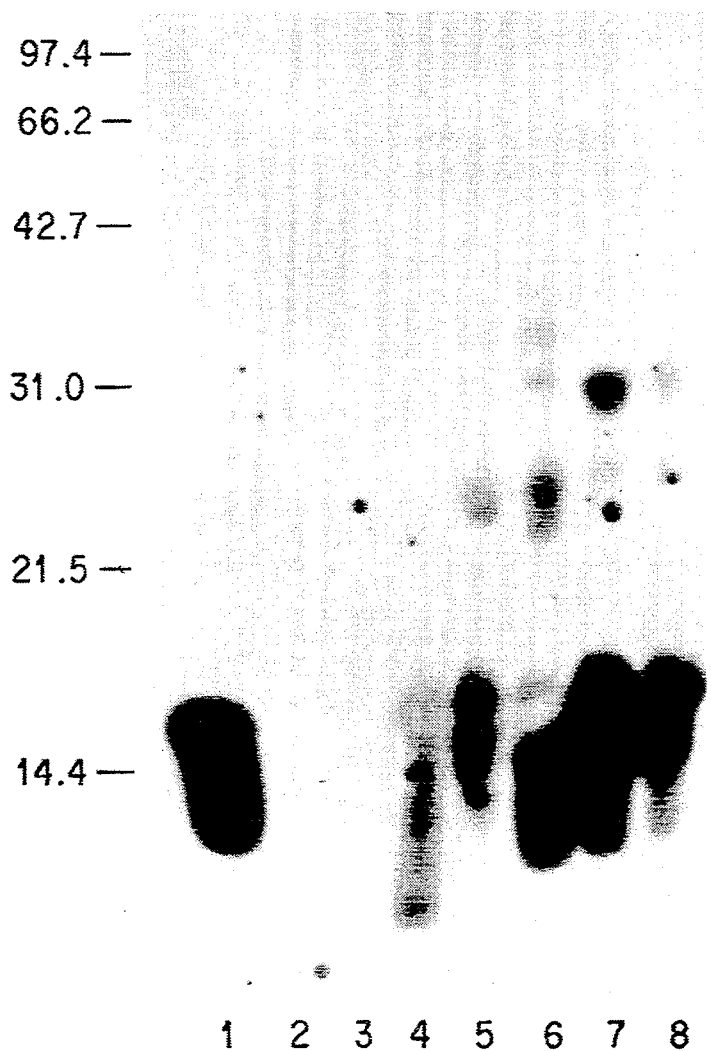
FIG. 10 is an autoradiogram of a 1D SDS-PAGE identifying specific proteins which bound to [$^{125}$I]-heparin in Example 7.

Reference is now made to FIG. 10 which identifies by autoradiography the specific proteins which bound [$^{125}$I]-heparin. The autoradiogram is representative of 3 separate preparations. In lane 1 is lysozyme, lane 2 is peak U1, lane 3 is U2, lane 4 is B1, lane 5 is B2, lane 6 is B3, lane 7 is B4, lane 8 is B5. Autoradiography verified that all the proteins in Peaks B1–B5 bound heparin while none in the flow-through fractions (U1 and U2) bound heparin. The higher affinity peaks (B3–B5) also were more intensely-labeled with [$^{125}$I]-heparin, confirming that these proteins had higher affinity for heparin. The basic 14 kD control protein, lysozyme, also bound heparin.

EXAMPLE 8

Identification of Seminal Plasma Proteins in Heparin Affinity HPLC Peaks Which Bind to Cauda Epididymal Spermatozoa

Radiolabeling of Heparin and Proteins

Heparin (5 mg.) was incubated in 1 ml. of 0.1M sodium tetraborate buffer, pH 9.0 with 1 mg. of Bolton Hunter reagent (Pierce Chemical Co., Rockford, Ill.) at 0° C. for 20 minutes with gentle agitation according to the methods described in Bolton and Hunter, 1973, "The Labeling of Proteins to High Specific Radioactivities by Conjugation to a $^{125}$I-Containing Acylating Agent," Biochem. J., 133:529–539; and Cardin, et al., 1984, Supra. The samples were centrifuged 15 minutes at 90,000 g. to remove the uncoupled, insoluble reagent. The supernatant was reacted under the same conditions with 1 mg. of Bolton Hunter reagent and centrifuged. To block any free reactive groups on the Bolton Hunter reagent, the supernatant was reacted with 0.4M glycine. Final separation of free from coupled Bolton Hunter reagent was performed by gel filtration chromatography on Sephadex G-25 (Pharmacia, Piscataway, N.J.) equilibrated in 50 MM NH$_4$HCO$_3$. The material eluting in the void volume was lyophilized.

The Bolton-Hunter derivative of heparin was radioiodinated with Iodogen (Pierce, Rockford, Ill.). Four mgs. of the derivative in 100 ul of 50 mM phosphate buffer were incubated in an Iodogen-coated test tube for 15 minutes with 1 mCi of Na$^{125}$I following the procedure recommended by the manufacturer. Uncoupled $^{125}$I was removed with a desalting column equilibrated in 40 mM Tris, 0.1% BSA, 0.01% azide, pH 7.35. Seminal plasma and control proteins (100 ug) were radioiodinated with 0.5 mCi of Na$^{125}$I in Iodogen-coated tubes in 50 mM phosphate buffer and uncoupled $^{125}$I was removed with a desalting column equilibrated in TALP.

Each of the radiolabeled protein peaks from the heparin-HPLC column or control proteins (33 ug) in 600 ul of TALP was concentrated to 100 ul by centrifugation in a Centricon-10 (Amicon, Danvers, Mass.). Cauda epididymal spermatozoa were flushed from 4–10 epididymides and 5×10$^6$ cells were added to each radiolabeled protein in Centricon microvials (final BSA concentration of 3.6%). The cells were incubated with the proteins for 20minutes at 22° C. The suspension was centrifuged at 300 g. for 10 minutes at 5° C. The pellet was resuspended in 500 ul of TALP and washed twice again. The final sperm pellet was solubilized in sample buffer for gel electrophoresis according to the process described in Laemmli, 1970, supra.

Radioiodinated seminal plasma heparin affinity peaks or control proteins (33 ug) were incubated with 5×10$^6$ epididymal sperm cells in 100 ul of TALP with 3.6% BSA for 20 minutes. The cells were washed three times and solubilized in SDS sample buffer for gel electrophoresis.

Figure 11:
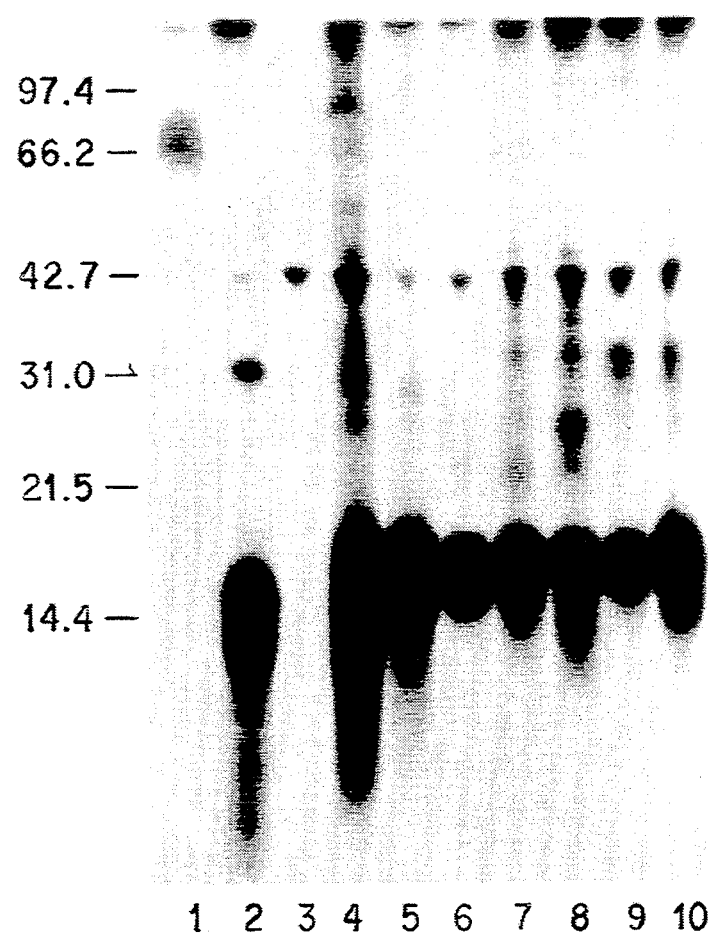
FIG. 11 is an autoradiogram identifying seminal plasma proteins in HPLC peaks which bound to epididymal sperm in Example 8.

Reference is made to FIG. 11 for the identification of seminal plasma proteins in heparin affinity HPLC peaks which bound to cauda epididymal sperm. Autoradiography identified the proteins which bound to epididymal sperm. In lane 1 are sperm incubated with BSA, lane 2 sperm with lysozyme, lane 3 ovalbumin lane 4 peak U1, lane 5 peak U2, lane 6 peak B1, lane 7 peak B2, lane 8 peak B3, lane 9 peak B4, lane 10 peak B5.

Seminal plasma proteins from all peaks bound to epididymal sperm, as did the control proteins ovalbumin and lysozyme. BSA labeling was minimal in medium with 3.6% unlabeled BSA. Therefore, cauda epididymal sperm may adsorb many proteins, including seminal plasma heparin-binding proteins and adsorption may be in a non-specific fashion.

EXAMPLE 9

Characterization of the Binding of Seminal Plasma Proteins to Epididymal Spermatozoa This example was designed to determine whether seminal plasma proteins bind to the plasma membranes of epididymal spermatozoa as peripheral membrane proteins or whether they were amphipathic and possibly integrated into the plasma membrane.

The ability of seminal plasma and control proteins to bind to bovine cauda epididymal spermatozoa was assessed in Example 8 using radioiodinated derivatives. Cauda epididymal spermatozoa were incubated with radioiodinated seminal plasma or control proteins as described previously except that the incubation was performed in 10 mM Tris-HCl, 150 mM NaCl, 6 mg/ml BSA, pH 7.35 (TBS) rather than TALP. The cells were washed 3 times, centrifuging at 300 g. for 10 minutes. The final pellet was resuspended in 0.5 ml. of hypertonic TBS (10 mM Tris, 400 mM NaCl, 6 mg/ml BSA, pH 7.35) and incubated for 5 minutes at room temperature according to the process described in Rifkin and Olson, 1985, "Characterization of Maturation-Dependent Extrinsic Proteins of the Rat Sperm Surface," *J. Cell Biol.*, 100:1582–1591. The cells were centrifuged at 300 g. for 10 minutes. The pellet was saved for Triton X-114 separation. The supernatant was aspirated and re-centrifuged at 1700 g. for 10 minutes to remove all cellular debris. Supernatant proteins were precipitated with 5% trichloroacetic acid at 4° C. for 1 hour and centrifuged at 3,000 g. for 5 minutes. Excess TCA was washed from the pellet with diethyl ether and the pellet was brought up in electrophoresis sample buffer. This was labeled as high ionic strength extract (HIS).

The cells, pre-extracted with hypertonic TBS, were phase separated to determine if the remaining seminal plasma proteins were amphipathic according to the method described in Bordier, 1981, "Phase Separation of Integral Membrane Proteins in Triton X-114 Solution," *J. Biol. Chem.*, 25,5:1604–1607. Triton X-114 (20 g. from Boehringer-Mannheim Biochemicals, Indianapolis, Ind.) and 16 mg. of butylated hydroxytoluene were washed 3 times with 980 ml. of TBS. The detergent concentration of the final stock was determined by absorbance at 254 nm using an extinction coefficient of 0.33 for a 0.05% (w/v) solution, as supplied by the manufacturer. The cells from the sperm pellet (in the previous paragraph) were resuspended in 200 ul of TBS with 1.0% Triton X-114. Each of the samples was layered over a cushion of 6% sucrose, 10 mM Tris, 150 mM NaCl, 0.06% Triton X-114 at 0° C. (Bordier, 1981, supra). Samples were warmed to 30° C. and centrifuged 3 minutes at 300 g. at room temperature. The upper aqueous phase was aspirated and adjusted to 0.5% with fresh Triton X-114, at 0° C. The mixture was overlaid on the same sucrose cushion, incubated 3 minutes at 30° C. and centrifuged 3 minutes at 300 g. The detergent phase was saved for electrophoresis and the aqueous phase was rinsed for the final time in a separate tube with 2% Triton X-114 at 0° C., incubated 3 minutes at 30° C. and centrifuged 3 minutes at 300 g. The aqueous phase was aspirated and the second detergent phase discarded. Triton X-114 or TBS was added to the aqueous or detergent phases, respectively, to bring the solutions to equivalent volumes and detergent concentrations. Proteins were TCA precipitated, as described above and resuspended in 100 ul of electrophoresis sample buffer. Equivalent volumes were loaded onto gels for electrophoresis and autoradiography.

Gel electrophoresis on slab gels was performed according to the method of Laemmli, 1970, supra, as described in Example 1, supra. Gels with radioiodinated proteins were subjected to autoradiography procedures described in Example 3, supra.

Reference is now made to FIGS. 12a and 12b for a characterization of the binding of seminal plasma proteins to cauda epididymal sperm. Radioiodinated seminal plasma heparin affinity peaks or control proteins (33 ug) were incubated with $5 \times 10^6$ cells in 100 ul of Tris buffered saline with 3.6% BSA for 20 minutes. The cells were washed 3 times and incubated with hypertonic TBS for 5 minutes. The cells were pelleted and the supernatant was TCA-precipitated, solubilized in 100 ul of SDS sample buffer containing 5% 2-mercaptoethanol and applied to gels for SDS-PAGE (FIG. 12a). The remaining pellet was phase-separated with Triton X-114 and the detergent phase was TCA-precipitated, solubilized in 100 ul of SDS sample buffer and characterized by SDS-PAGE under reducing conditions. Equivalent volumes of hypertonic extract and detergent phase were applied to the gels and autoradiography was used to visualize the labeled proteins (FIG. 12b). Exposure times of 36 hours and 400 hours were required for autoradiograms of hypertonic extract and the sperm detergent phase, respectively, and the autoradiograms were representative of 3 preparations.

Autoradiographic analysis of the supernatant (36 hour exposure) indicated that the major proteins in seminal plasma (14–18 kD) were removed from sperm by incubation in hypertonic medium (FIG. 12a). The less prominent seminal plasma proteins were not observed, even in overexposed autoradiograms.

Amphipathic proteins, dissolved at 0° C. in Triton X-114, separate into the detergent phase upon warming to 30° C. (Bordier, 1981, supra). Following incubation with the iodinated seminal plasma proteins and hypertomic TBS removal of peripheral proteins, the sperm were solubilized in Triton X-114. The sperm aqueous phase contained proteins similar to those observed in the hypertonic extraction but present at greatly reduced amounts requiring a 400 hour autoradiographic exposure. The sperm detergent phase contained only small amounts of the 14–18 kD proteins, which also required an exposure time of 400 hours to visualize by autoradiography (FIG. 12b). Therefore, the seminal plasma proteins which bound to sperm were peripheral membrane proteins and were not amphipathic.

EXAMPLE 10

Effect of Seminal Plasma Proteins on Heparin-Induced Capacitation

This example was designed to determine if the seminal plasma heparin-binding proteins would, when added to cauda epididymal sperm, allow sperm to be capacitated by heparin and undergo acrosome reactions when zonae pellucidae were added.

Bovine spermatozoa were pooled from 2–3 normal ejaculates (motility greater than 80%), washed twice at 300 g. for 10 minutes and diluted to $5 \times 10^7$ cells/ml in dmTALP (100 mM NaCl, 3.1 mM KCl, 1.5 mM $MgCl_2$, 2.1 mM $CaCl_2$, 0.29 mM $KH_2PO_4$, 10 mM $NaHCO_3$, 25 mM HEPES, 1 mM Na pyruvate, 21.6 mM lactate, 6 mg/ml BSA (essentially fatty acid free, Sigma Chemical Co., St. Louis, Mo.), 100 units/ml penicillin, 100 ug/ml streptomycin, pH 7.4 at 39° C.). The medium was made fresh and filtered (0.2 um) prior to use. Sperm were supplemented with 0 or 10 ug/ml of heparin (sodium salt of porcine intestinal mucosa, Calbiochem, LaJolla, Calif.) and 500 ul of the suspension were incubated for 5 hours in $12 \times 75$ capped culture tubes at 39° C. (body temperature in the cow) in a water bath at 80 oscillations per minute.

Cauda epididymal sperm were collected with dmTALP and diluted to $10^8$/ml without washing. Bovine seminal plasma was collected from 3 vasectomized bulls and pooled. One hundred ul of seminal plasma (Florman and First, 1988b, supra and 150 ul of dmTALP were added to 250 ul of the epididymal sperm suspension. Protein-containing peaks from the heparin affinity HPLC separation (a recombined sample of all the peaks or each individual peak) were dissolved in 250 ul of dmTALP. The amount of each protein peak added to the pooled sample or added individually was based on the relative proportion of total protein accounted for by each chromatography peak, as assessed by absorbance at 280 nm (see Table 1, Example 5). Two hundred fifty ug of total protein were added in the recombined sample and the amount of protein added from each peak was a specific fraction of that total (Table 1). Lysozyme and ovalbumin were used as control proteins. The proteins and sperm were mixed for 20 minutes at 22° C. and then the cells were washed twice at 300 g for 10 minutes. They were resuspended in 500 ul of dmTALP with 0 or 10 ug/ml of heparin. The cells were incubated for 5 hours in $12 \times 75$ culture tubes at 39° C. in a water bath at 80 oscillations per minute.

Alternatively, 100 ul of seminal plasma was added to epididymal sperm after 4 hours of incubation with 0 or 10 ug/ml of heparin. Following a 20 minute incubation, the cells were washed twice and resuspended in dmTALP with 0 or 10 ug of heparin.

Zonae pellucidae were prepared from ovaries by screen separation, homogenization and Percoll density gradient centrifugation as described by Florman and First, 1988a, supra. Soluble extracts were prepared by heating in dilute acetic acid (pH 2.5) and the preparation was lyophilized and solubilized in dmTALP (1 mg. protein/ml) just prior to use.

After 5 hours of incubation, 12.5 ul of the sperm suspension were added to 12.5 ul of soluble zonae pellucidae or control (transferrin or beta-globulin) protein (final zonae or control concentration of 50 ng/ul) in 500 ul microtubes at 39° C. in triplicate. This concentration of zonae pellucidae induced the maximal frequency of acrosome reactions (Florman and First, 1988a, supra). Following 30 minutes of incubation, motility was estimated by bright field microscopy and sperm suspensions were smeared and air-dried on microscope slides. The cells were stained for acrosome reactions using a procedure previously validated by transmission electron microscopy and in vitro fertilization (Lenz, et al., 1983a, supra). To reduce possible photodegradation, the stains were made fresh for each assay. Spermatozoa (200/slide) were examined at a magnification of 400× for the acrosome reaction which was indicated by the absence of a cherry red apical rim (Lenz, et al., 1983a, supra). This assay was performed twice, in triplicate, and the results were subjected to analysis of variance (Statistical Analysis System, SAS Institute, Inc., Cary, N.C.) using, as main effects, heparin concentration, capacitation protein, acrosome reaction protein and type of sperm (ejaculated vs. epididymal). Comparisons of individual means were made using Tukey's studentized range test within SAS (alpha less than 0.05).

Protein determinations were made using the bicinchoninic acid assay (BCA assay, Pierce Chemical Co., Rockford, Ill.) employing BSA as a standard. Membrane proteins were solubilized in 1% SDS prior to assay.

This experiment was designed to determine if the seminal plasma heparin-binding proteins would, when added to cauda epididymal sperm, allow sperm to be capacitated by heparin and undergo acrosome reactions when zonae pellucidae were added. Ejaculated sperm were incubated 5 hours with 0 or 10 ug/ml of heparin (to stimulate capacitation) then exposed to solubilized zonae pellucidae, transferrin or beta-globulin (control proteins) 30 minutes to induce acrosomal exocytosis in capacitated sperm. None of the treatments were cyctotoxic, since motility was not affected. Heparin caused significant head-to-head agglutination of sperm while no agglutination was observed in the absence of heparin. Reference is now made to the following Table 2 which discloses the effects of reconstitution of epididymal sperm with seminal plasma on heparin-induced capacitation:

TABLE 2

| Sperm Source | Heparin (10 ug/ml) | Capacitation Protein* | AR Protein** | AR %§ |
|---|---|---|---|---|
| Ejaculated | — | Controls | Controls | $14.3^a$ |
| Ejaculated | + | Controls | Controls | $20.1^a$ |
| Ejaculated | — | Controls | ZP# | $20.3^a$ |
| Ejaculated | + | Controls | ZP | $41.7^b$ |
| Epididymal | — | Controls | Controls | $10.2^a$ |
| Epididymal | — | Controls | ZP | $10.3^a$ |
| Epididymal | + | Controls | Controls | $11.9^a$ |
| Epididymal | + | Controls | ZP | $14.5^a$ |
| Epididymal | — | SP@ | Controls | $7.3^a$ |
| Epididymal | — | SP | ZP | $13.5^a$ |
| Epididymal | + | SP | Controls | $17.7^a$ |
| Epididymal | + | SP | ZP | $39.4^b$ |
| Epididymal | + | SP added after 4 hours | Controls | $31.9^b$ |
| Epididymal | + | SP added after 4 hours | ZP | $32.2^b$ |

*Capacitation protein controls included no additional protein or 100 ug/ml of ovalbumin or lysozyme.
**AR = acrosome reaction. AR controls were no added protein or 50 ng/ul of transferrin or beta-globulin.
§ AR frequences with different superscripts differ (P is less than 0.05).
ZP = zona pellucida
@ SP = seminal plasma Acrosomal exocytosis was stimulated in 41.7% of the ejaculated cells following incubation with heparin and exposure to zonae pellucidae, while acrosome reactions in control incubations with transferrin or beta-globulin were at 20.3%. Incubation with heparin was required for zonae pellucidae-induction of exocytosis. Epididymal sperm required a 20 minute exposure to seminal plasma (100 ul), incubation with heparin for 4–5 hours and addition of zonae to achieve frequencies of acrosome reactions similar (39.4%) to ejaculated sperm exposed to zonae. Epididymal sperm exposed to ovalbumin or to lysozyme (which binds heparin and binds to sperm, FIGS. 10 and 11) did not undergo an increase in zonae-induced exocytosis. Seminal plasma-treated epididymal sperm exposed to transferrin or beta-globulin rather than zonae pellucidae had background frequencies of exocytosis. Thus, a 20 minute seminal plasma exposure, a 4-5 hour incubation with heparin and a 30 minute exposure to soluble zonae pellucidae proteins are required for maximal rates of acrosomal exocytosis in epididymal sperm.

To discern if seminal plasma was acting during the capacitation step or the acrosome reaction, epididymal sperm were incubated 4 hours with heparin, exposed to seminal plasma, incubated for 20 minutes and washed. Seminal plasma reversed the head-to-head agglutination of sperm caused by heparin. Intrinsic frequencies of acrosome reactions were higher in this treatment, presumably due to rupture of an unstable acrosome in the washing step. Solubilized zonae pellucidae did not stimulate acrosomal exocytosis in sperm exposed to seminal plasma just prior to addition of zonae, compared to control proteins (transferrin and beta-globulin). These data suggest that exposure to a seminal plasma component is required or the 4-5 hour capacitation time. Alternatively, an inhibitory component of seminal plasma may be present in seminal plasma which requires 5 hours for removal from the cell. Either of these changes are time-dependent events which may be associated with capacitation (Yanagimachi, 1981, "Mechanisms of Fertilization in Mammals," *In Fertilization and Embryonic Development In Vitro*, L. Mastroianni and J. D. Biggers, editors, Plenum Press, N.Y., 81–183 ).

The effects of seminal plasma heparin-binding proteins on zonae pellucidae-induced acrosomal exocytosis were examined. Proteins in isolated peaks from the heparin affinity column (U1, U2, B1–B5) were added to epididymal sperm in amounts proportional to the amount of each peak in whole seminal plasma (Table 1). A proportional pool of all peaks was added to epididymal sperm at a concentration (0.5 mg. protein/ml) reported to be twice the concentration of total protein required for maximal activity (Florman and First, 1988b, supra).

Reference is made to the following Table 3 which describes the effect of seminal plasma heparin-binding proteins on the potentiation of heparin-induced capacitation in epididymal sperm:

TABLE 3

| Capacitation Protein | AR Protein* | Protein Added (ug) | AR %§ |
|---|---|---|---|
| Pooled Fractions | Controls | 250 | 13.0$^a$ |
| Pooled Fractions | ZP | 250 | 32.1$^b$ |
| Peak U1 | Controls | 97.5 | 16.4$^a$ |
| Peak U1 | ZP | 97.5 | 20.0$^a$ |
| Peak U2 | Controls | 83.0 | 15.2$^a$ |
| Peak U2 | ZP | 83.0 | 20.0$^a$ |
| Peak B1 | Controls | 18.8 | 14.4$^a$ |
| Peak B1 | ZP | 18.8 | 30.9$^b$ |
| Peak B2 | Controls | 23.8 | 15.1$^a$ |
| Peak B2 | ZP | 23.8 | 34.7$^b$ |
| Peak B3 | Controls | 11.8 | 14.7$^a$ |
| Peak B3 | ZP | 11.8 | 36.2$^b$ |
| Peak B4 | Controls | 11.0 | 13.1$^a$ |
| Peak B4 | ZP | 11.0 | 33.5$^b$ |
| Peak B5 | Controls | 4.3 | 13.2$^a$ |
| Peak B5 | ZP | 4.3 | 33.7$^b$ |

*AR = acrosome reaction. AR controls included no added protein or 50 ng/ul of transferrin or beta-globulin.
§ Means with different superscripts differ (P is less than 0.05).

A 20 minute exposure to the pooled fractions stimulated a 2 to 3-fold increase in zona-induced acrosomal exocytosis. Incubation with heparin was required for the pooled fractions to display activity. There was no significant potentiation of zonae pellucidae-induced acrosome reactions by Peak U1 or U2. However, heparin-binding peaks B1 through B5 all had stimulatory activity. Frequencies of acrosomal exocytosis ranged from 30.9 to 36.2%, approximately a 2 to 3-fold enhancement compared to control proteins (Tables 2 and 3). Maximal stimulation was induced by proteins in Peak B3. Each heparin-binding peak was able to induce frequencies of acrosomal exocytosis comparable to that of the pooled fractions. However, the amount of protein added to epididymal sperm was lowest in peaks B3–B5. Therefore, the activity/unit protein was highest in those peaks.

It is understood that the invention is not confined to the particular construction and arrangement herein illustrated and described, but embraces such modified forms thereof as come within the scope of the following claims:

What is claimed is:

1. An aqueous solution having spermatozoa capacitating ability consisting essentially of a heparin-binding protein isolatable from seminal plasma and separated from other heparin-bending proteins and having one of the following characteristics:
   a) a molecular weight of 13 (kD-SDS PAGE) and an isoelectric point between 6.5 and 7.5;
   b) a molecular weight of 14–16 (kD-SDS PAGE) and an isoelectric point between 4.1 and 8;
   c) a molecular weight of 24 (kD-SDS PAGE) and an isoelectric point between 6 and 8;
   d) a molecular weight of 30–35 (kD-SDS PAGE) and isoelectric point between 5 and 6.5.

2. An aqueous solution having spermatozoa capacitating ability consisting essentially of a heparin-binding protein isolatable from seminal plasma and separated from other heparin-binding proteins and having one of the following characteristics;
   a) a molecular weight of 14–16 (kD-SDS PAGE) and an isoelectric point between 4.1 and 5.1;
   b) a molecular weight of 31 (KD-SDS PAGE) and an isoelectric point between 5 and 6.5.

3. A method of isolating heparin-binding proteins from a first seminal plasma, purifying the heparin-binding proteins and introducing heparin-binding proteins to a second seminal plasma, comprising:
   a) providing the first seminal plasma which contains heparin-binding proteins;
   b) treating the first seminal plasma using affinity chromatography employing heparin moieties linked to an insoluble support matrix to bind the heparin-binding proteins to the matrix;
   c) eluting the bound protein with an increasing gradient of substance having a higher affinity to the matrix than the bound protein to remove the bound protein from the matrix;
   d) collecting liquid fractions containing substantially purified heparin-binding proteins;
   e) isolating the substantially purified heparin-binding proteins according to heparin-binding affinity constants; and
   f) adding at least one of the isolated substantially purified heparin-binding proteins to the second seminal plasma.

4. The method of claim 3 wherein step c) employs a salt gradient mobile phase of increasing salt concentration.

5. The method of claim 3 wherein the affinity chromatography is low pressure liquid chromatography.

6. The method of claim 3 wherein the affinity chromatography is high pressure liquid chromatography.

7. A method for enhancing acromosomal reaction in sperm cells comprising introducing a composition to the sperm cells, wherein the composition is isolatable from seminal plasma, is comprised of heparin-binding proteins, and has spermatozoa capacitating ability, and wherein the composition has properties selected from the group consisting of:

B1:
  a) molarity of NaCl required for elution: 0.15,
  b) molecular weights (kD): 13, 14–16, 24, 30–35,
  c) isoelectric points: 6.5–7.5, 4.1–8.0, 6–8, 5–6.5;

B2:
  a) molarity of NaCl required for solution: 0.54,
  b) molecular weights (kD): 14–16, 24, 30–35,
  c) isoelectric points: 4.1–8.0, 6–8, 5–6.5;

B3:
  a) molarity of NaCl required for solution: 0.66,
  b) molecular weights (kD): 14–16, 24, 30–35,
  c) isoelectric points: 4.1–8.0, 6–8, 5–6.5;

B4:
  a) molarity of NaCl required for solution: 0.74,
  b) molecular weights (kD): 14–16, 24, 31,
  c) isoelectric points: 4.1–5.1, 6–8, 5–6.5; and B5:
  a) molarity of NaCl required for elution: 0.90,
  b) molecular weights (kD): 14–16, 24, 31,
  c) isoelectric points: 4.1–5.1, 6–8, 5–6.5.

8. A method of enhancing the fertility of the sperm calls of a mammal comprise introducing to the sperm cells one or more compositions having spermatozoa capacitating ability comprising heparin-binding proteins isolatable from terminal plasma and having properties selected from the group consisting of:

B1:
  a) molarity of NaCl required for elution: 0.15,
  b) molecular weights (kD): 13, 14–16, 24, 30–35,
  c) isoelectric points: 6.5–7.5, 4.1–8.0, 6–8, 5–6.5;

B2:
  a) molarity of NaCl required for solution: 0.54,
  b) molecular weights (kD): 14–16, 24, 30–35,
  c) isoelectric points: 4.1–8.0, 6–8, 5–6.5;

B3:
  a) molarity of NaCl required for elution: 0.66,
  b) molecular weights (kD): 14–16, 24, 30–35,
  c) isoelectric points: 4.1–8.0, 6–8, 5–6.5;

B4:
  a) molarity of NaCl required for elution: 0.74,
  b) molecular weights (kD): 14–16, 24, 31,
  c) isoelectric points: 4.1–5.1, 6–8, 5–6.5; and B5:
  a) molarity of NaCl required for elution: 0.90,
  b) molecular weights (kD): 14–16, 24, 31,
  c) isoelectric points: 4.1–5.1, 6–8, 5–6.5.

* * * * *

UNITED STATES PATENT AND TRADEMARK OFFICE
CERTIFICATE OF CORRECTION

PATENT NO : 5,434,139
DATED : July 18, 1995
INVENTOR(S): Roy L. Ax et al.

It is certified that error appears in the above-identified patent and that said Letters Patent is hereby corrected as shown below:

Column 23, line 15, delete "solution" and add --elution-- therefor.

Column 23, line 19, delete "solution" and add --elution-- therefor.

Column 23, line 23, delete "solution" and add --elution-- therefor.

Column 24, line 3, delete "comprise" and add --comprising-- therefor.

Column 24, line 6, delete "terminal" and add --seminal-- therefor.

Column 24, line 13, delete "solution" and add --elution-- therefor.

Signed and Sealed this

Seventeenth Day of March, 1998

*Attest:*

BRUCE LEHMAN

*Attesting Officer*  Commissioner of Patents and Trademarks